(12) United States Patent
Sakurai et al.

(10) Patent No.: US 8,315,883 B2
(45) Date of Patent: Nov. 20, 2012

(54) EXAMINATION-ITEM-SELECTION DEVICE, AN EXAMINATION-ITEM-SELECTION METHOD, AND AN EXAMINATION-ITEM-SELECTION PROGRAM

(75) Inventors: Yasuo Sakurai, Otawara (JP); Shigeharu Ohyu, Yaita (JP); Takuzo Takayama, Otawara (JP); Mariko Shibata, Yokohama (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 427 days.

(21) Appl. No.: 11/859,926

(22) Filed: Sep. 24, 2007

(65) Prior Publication Data

US 2008/0076976 A1 Mar. 27, 2008

(30) Foreign Application Priority Data

Sep. 25, 2006 (JP) ................................. 2006-259334

(51) Int. Cl.
*G06Q 10/00* (2012.01)
(52) U.S. Cl. ..................... 705/2; 705/3; 707/9
(58) Field of Classification Search ........................ 705/2
See application file for complete search history.

(56) References Cited

U.S. PATENT DOCUMENTS

| 5,551,436 A * | 9/1996 | Yago .............................. 600/483 |
| 6,754,655 B1 * | 6/2004 | Segal .................................... 1/1 |
| 7,376,574 B2 * | 5/2008 | Toan et al. ......................... 705/4 |
| 7,650,290 B2 * | 1/2010 | Van Kalken et al. ............. 705/2 |

FOREIGN PATENT DOCUMENTS

| JP | 2002-183647 | 6/2002 |
| JP | 2003-38448 | 2/2003 |

* cited by examiner

Primary Examiner — Hiep V Nguyen
(74) Attorney, Agent, or Firm — Oblon, Spivak, McClelland, Maier & Neustadt, L.L.P.

(57) ABSTRACT

An examination-item database storing a plurality of types of examination items capable of examining a predetermined disease and attributes of these examination items so as to correspond to one another is prepared, the degree of risk for the predetermined disease is calculated based on individual physical information, a criterion for selection of an examination item for examining the predetermined disease is generated in accordance with the calculated degree of risk, and an examination item having an attribute meeting the selection criterion is searched out from the examination-item database. In addition, the calculated degree of risk and the examination-item database are displayed so as to correspond to the predetermined disease. This makes it possible to perform the optimal examination for each individual in accordance with the degree of risk, thereby improving the efficiency of detection of a disease. Moreover, reduction of superfluous examinations makes it possible to reduce physical and psychological burdens imposed on a patient by examinations.

7 Claims, 24 Drawing Sheets

FIG. 2

| | INFORMATION ON TYPE OF PHYSICAL INFORMATION j | INFORMATION ON TYPE OF NORMALIZATION FUNCTION fj(x) | | OFFSET VALUE(a) | SCALE VALUE(b) | EXECUTION FILE OF NORMALIZATION FUNCTION fj(x) |
|---|---|---|---|---|---|---|
| j=1 | ANGIOTENSIN CONVERTING ENZYME (ACE) ALTER | $f_1(X)$ | BINARY | 0 | 1 | f1= for X=1<br>0 for X=0 |
| j=2 | BLOOD GLUCOSE LEVEL | $f_2(X)$ | STEP FUNCTION | 200 | 1 | f2=step[(X-b)/a] |
| j=3 | TOTAL CHOLESTEROL | $f_3(X)$ | SIGMOID FUNCTION | 180 | 100 | f3=sigmoid[(X-b)/a] |
| j=4 | SMOKING | $f_4(X)$ | LINEAR FUNCTION | 0 | | f4=(X-b)/a |
| j=5 | BLOOD PRESSURE | $f_5(X)$ | EXPONENTIAL FUNCTION | 50 | 120 | f5=1-exp[(X-b)/a] |
| j=6 | BLOOD PRESSURE VALUE, BLOOD GLUCOSE LEVEL | $f_6(X)$ | PRODUCT (f2,f5) | | | f6=f2·f5 |
| j=7 | LOGICAL PRODUCT OF ANGIOTENSIN-CONVERTING ENZYME (ACE) ALTER- BLOOD GLUCOSE LEVEL | $f_7(X)$ | LOGICAL PRODUCT (f1,f5) | | | f7=f1 and f5 |

FIG. 3

| VARIABLE fj | CORRELATION COEFFICIENT Aij | | | |
|---|---|---|---|---|
| | DIABETES (i=1) | COLON CANCER (i=2) | ISCHEMIC DISEASE (i=3) | |
| f0 (BASIC MORBIDITY RATE) | A10=0.00202 | A20=0.00102 | A30=0.00022 | |
| f1 | A11=0.00012 | | | |
| f2 | A12=0.00024 | | | |
| f3 | A13 | | | |
| f4 | A14 | | | |
| f5 | | | | |
| f6 | | | | |
| f7 | | | | |
| | | | | |

FIG. 4A

| PHYSICAL INFORMATION j ||||||||||
|---|---|---|---|---|---|---|---|---|---|
| INFORMATION ON TYPE OF PHYSICAL INFORMATION j | | VALUE X |||||||||
| SEX | | M |||||||||
| AGE | | 58 |||||||||
| BLOOD TYPE | | B |||||||||
| | | 2012 | 2011 | 2010 | 2009 | 2008 | 2007 | 2006 | |
| BODY HEIGHT | j=1 | 170.5 | 170.5 | 170.5 | 170.5 | 170.5 | 170.5 | 170.5 | |
| BODY WEIGHT | j=2 | 63.2 | 64 | 63.2 | 64 | 64.6 | 64 | 63.2 | |
| SYSTOLIC BLOOD PRESSURE | j=3 | 112 | 115 | 112 | 116 | 125 | 133 | 129 | |
| DIASTOLIC BLOOD PRESSURE | j=4 | 89 | 60 | 62 | 62 | 63 | 60 | 59 | |
| DEGREE OF OBESITY | j=5 | 4.1 | | | | | | | |
| BMI | j=6 | 23 | 22.9 | 23.8 | 22.9 | 23.5 | 23.5 | 23.1 | |
| BODY FAT PERCENTAGE | j=7 | 19 | 19 | 18.5 | 15.5 | 15.5 | 14.5 | 14 | |
| VISUAL ACUITY | j=8 | 1.0/1.0 | 1.0/1.0 | 1.0/1.0 | 1.0/1.0 | 1.0/1.0 | 1.0/0.9 | 1.0/1.0 | |
| PROTEIN (URINE) | j=9 | + | + | − | − | − | − | − | |
| SUGAR (URINE) | j=10 | + | + | − | − | − | − | − | |
| OCCULT BLOOD (URINE) | j=11 | − | − | − | − | − | − | − | |
| WHITE-BLOOD-CELL COUNT | j=12 | 6120 | 6280 | 5990 | 6120 | 6020 | 6160 | 6310 | |
| RED-BLOOD-CELL COUNT | j=13 | 448 | 424 | 411 | 451 | 458 | 423 | 444 | |
| HEMOGLOBIN CONTENT | j=14 | 14.5 | 12.9 | 15 | 14.3 | 14.9 | 14.1 | 14.3 | |
| HEMATOCRIT | j=15 | 42 | 44 | 45.5 | 50 | 44 | 44.8 | 44.7 | |
| GOT | j=16 | 18 | 18 | 21 | 18 | 20 | 18 | 19 | |
| GPT | j=17 | 16 | 17 | 20 | 20 | 17 | 19 | 16 | |
| γ-GTP | j=18 | 14 | 15 | 20 | 19 | 21 | 20 | 18 | |
| AL-P | j=19 | 163 | 185 | 177 | 164.5 | 170.1 | 180.5 | 172.4 | |
| TOTAL CHOLESTEROL | j=20 | 171 | 170.5 | 168.5 | 165.5 | 168.5 | 166.4 | 172.9 | |
| NEUTRAL FAT | j=21 | 60 | 50 | 50 | 55 | 50 | 52 | 53 | |
| HDL CHOLESTEROL | j=22 | 59 | 60 | 62 | 54.4 | 54.3 | 56.7 | 68 | |
| URIC ACID | j=23 | 8.2 | 7.5 | 7.2 | 8.4 | 7.3 | 7.3 | 6.9 | |
| CREATININE | j=24 | 1 | 1.12 | 0.95 | 1.05 | 1 | 1 | 1.1 | |
| BLOOD GLUCOSE | j=25 | 65 | 60 | 70 | 71 | 68 | 64 | 62 | |
| HbA1e | j=26 | 5.1 | 5.5 | 5.3 | 5.5 | 5.1 | 5.2 | 5.4 | |

FIG. 4B

| PHYSICAL INFORMATION j |||||||||||
|---|---|---|---|---|---|---|---|---|---|---|
| INFORMATION ON TYPE OF PHYSICAL INFORMATION j | VALUE X ||||||||||
| NAME OF A DISEASE | j=27 | DATE OF JUDGMENT | METHOD OF TREATMENT | PROGNOSIS | ADMINISTERED MEDICAL AGENTS ||||||
| APPENDICITIS | j=28 | 1986.06.24 | SURGERY | COMPLETE RECOVERY | MEDICAL AGENTS A | 50mg | 1986.17.01 | 50mg | 1986.07.07 ||
| ||||| MEDICAL AGENTS C | 25mg | 1986.17.01 ||||
| RIGHT ANKLE SPRAIN | j=29 | 1991.12.15 | PRESERVATIVE TREATMENT (PHYSICAL THERAPY, ETC) | COMPLETE RECOVERY | MEDICAL AGENTS B | 50mg | 1991.12.15 ||||
| CHOLELITHIASIS | j=30 | 2010.07.01 | SURGERY | COMPLETE RECOVERY | MEDICAL AGENTS A | 75mg | 2010.07.07 ||||
| ALLERGIES | j=31 | NONE |||||||||
| BLOOD-BIOCHEMICAL EXAMINATIONS (AAA) | j=32 | 3.2 | 1986.06.30 |||||||
| BLOOD-BIOCHEMICAL EXAMINATIONS (BBB) | j=33 | — | 1986.06.30 |||||||
| BLOOD-BIOCHEMICAL EXAMINATIONS (CCC) | j=34 | 2.25 | 1986.06.30 |||||||
| BLOOD-BIOCHEMICAL EXAMINATIONS (DDD) | j=35 | 2.19 | 1990.10.30 |||||||
| BLOOD-BIOCHEMICAL EXAMINATIONS (DDD) | j=36 | 3.51 | 2005.05.15 |||||||
| GENE | j=37 | MULTIPLE-CLASSIFICATION TYPE |||||||||
| CYP1A1 | j=38 | A - TYPE |||||||||
| GSTM1 | j=39 | + - TYPE |||||||||
| CYP1A2 | j=40 | B - TYPE |||||||||
| GYP1B1 | j=41 | − - TYPE |||||||||
| CYP2A6 | j=42 | − - TYPE |||||||||
| GYP2D6 | j=43 | C - TYPE |||||||||

FIG. 6

| DISEASE i | DISEASE-DEVELOPMENT PROBABILITY WITHIN NEXT 3 YEARS | DISEASE-DEVELOPMENT PROBABILITY WITHIN NEXT 5 YEARS |
|---|---|---|
| DIABETES | 1% | 1.70% |
| COLON CANCER | 0.50% | 0.90% |
| ISCHEMIC DISEASE | 0.50% | 1.50% |
| LUNG CANCER | 0.40% | 0.50% |
| PANCREATIC CANCER | 0.30% | 0.32% |
| MEDULLARY CANCER | 0.00% | 0.00% |

FIG. 7

| DISEASE i | | COLON CANCER | | |
|---|---|---|---|---|
| | EXAMINATION-ACCURACY RANK R | NUMBER OF YEARS t | SECTION DIV OF DISEASE-DEVELOPMENT PROBABILITY | |
| i=1 | RANK A | 3 YEARS | 3% | MORE |
| | RANK B | 3 YEARS | 1% | MORE |
| | RANK B | 5 YEARS | 1.50% | MORE |
| | RANK C | 3 YEARS | 0.50% | MORE | 3% | LESS |
| | | | 1% | LESS |
| ... | | | | |

| DISEASE i | | | | |
|---|---|---|---|---|
| | EXAMINATION-ACCURACY RANK R | NUMBER OF YEARS t | SECTION DIV OF DISEASE-DEVELOPMENT PROBABILITY | |
| i=2 | RANK A | ... | ... | ... |
| | RANK B | ... | ... | ... |
| | RANK C | 3 YEARS | 0.50% | MORE | 1% | LESS |

FIG. 8

| DISEASE i | EXAMINATION-ITEM (EXAMINATION-ACCURACY RANK C) | EXAMINATION-ITEM (EXAMINATION-ACCURACY RANK B) | EXAMINATION-ITEM (EXAMINATION-ACCURACY RANK A) |
|---|---|---|---|
| DIABETES | — | BIOCHEMICAL EXAMINATION (DIABETES) | — |
| COLON CANCER | BIOCHEMICAL EXAMINATION (COLON CANCER MARKER) | COLONOSCOPY | LARGE-INTESTINE-TISSUE BIOPSY |
| ISCHEMIC DISEASE | BIOCHEMICAL EXAMINATION (IHD) | ECHOCARDIOGRAPHY | X-RAY ANGIOGRAPHIC EXAMINATION |
| LUNG CANCER | BIOCHEMICAL EXAMINATION (LUNG CANCER MARKER) | MR IMAGE EXAMINATION (LUNG CANCER MARKER) | LUNG-TISSUE BIOPSY |
| PANCREATIC CANCER | BIOCHEMICAL EXAMINATION (PANCREATIC CANCER MARKER) | MR IMAGE EXAMINATION (PANCREATIC CANCER MARKER) | — |
| MEDULLARY CANCER | — | BIOCHEMICAL EXAMINATION (MEDULLARY CANCER MARKER A) / BIOCHEMICAL EXAMINATION (MEDULLARY CANCER MARKER B) | — |

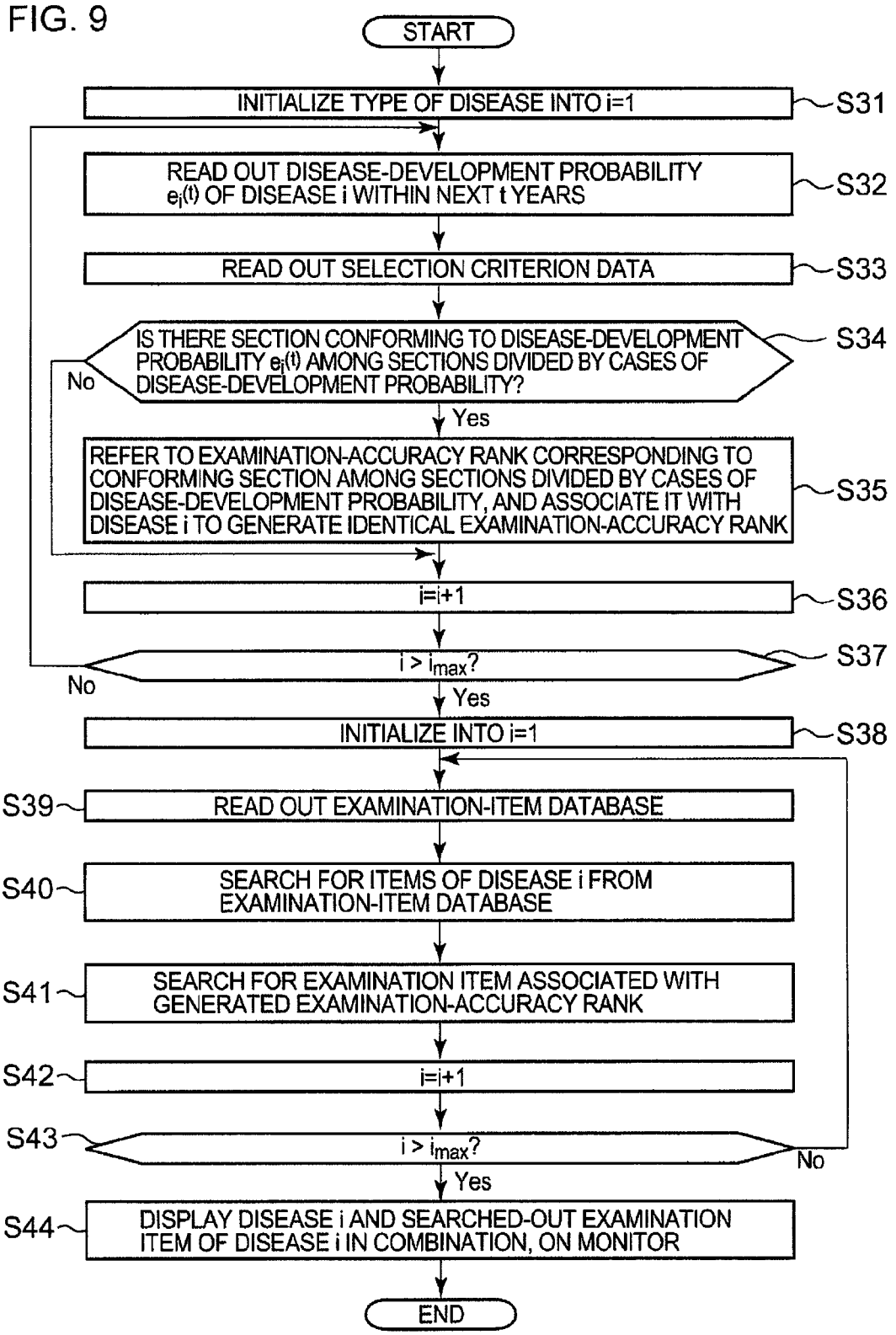

FIG. 10

RECOMMENDED EXAMINATION ITEMS FOR MR. KOIZUMI ARE AS FOLLOWS.

| DISEASE i | RECOMMENDED EXAMINATION ITEMS |
|---|---|
| DIABETES | UNNECESSARY |
| COLON CANCER | COLONOSCOPY |
| ISCHEMIC DISEASE | UNNECESSARY |
| LUNG CANCER | LUNG-TISSUE BIOPSY |
| PANCREATIC CANCER | BIOCHEMICAL EXAMINATION (PANCREATIC CANCER MARKER) |
| MEDULLARY CANCER | UNNECESSARY |

[ SETTLE ]  [ RE-SELECT ]  [ CANCEL ]

FIG. 11

| DISEASE i | EXPENDITURE INFORMATION Ct |
|---|---|
| COLON CANCER | ¥320,000 |
| ISCHEMIC DISEASE | ¥250,000 |
| LUNG CANCER | ¥500,000 |
| PANCREATIC CANCER | ¥700,000 |
| MEDULLARY CANCER | ¥1,200,000 |

FIG. 12

| DISEASE i | EXAMINATION-ACCURACY RANK R (RANK C) / COST Ce | EXAMINATION-ACCURACY RANK R (RANK B) / COST Ce | EXAMINATION-ACCURACY RANK R (RANK A) / COST Ce |
|---|---|---|---|
| DIABETES | — | BIOCHEMICAL EXAMINATION (DIABETES) ¥200 | — |
| COLON CANCER | BIOCHEMICAL EXAMINATION (COLON CANCER MARKER) ¥1500 | COLONOSCOPY ¥9000 | LARGE-INTESTINE-TISSUE BIOPSY ¥10000 |
| ISCHEMIC DISEASE | BIOCHEMICAL EXAMINATION (IHD) ¥1000 | ECHOCARDIOGRAPHY ¥5000 | X-RAY ANGIOGRAPHIC EXAMINATION ¥9000 |
| LUNG CANCER | BIOCHEMICAL EXAMINATION (LUNG CANCER MARKER) ¥1500 | MR IMAGE EXAMINATION (LUNG CANCER MARKER) ¥7000 | LUNG-TISSUE BIOPSY ¥10000 |
| PANCREATIC CANCER | BIOCHEMICAL EXAMINATION (PANCREATIC CANCER MARKER) ¥3000 | MR IMAGE EXAMINATION (PANCREATIC CANCER MARKER) ¥9000 | — |
| MEDULLARY CANCER | — | BIOCHEMICAL EXAMINATION (MEDULLARY CANCER MARKER A) ¥10000 / BIOCHEMICAL EXAMINATION (MEDULLARY CANCER MARKER B) ¥11000 | — |

FIG. 14A

RECOMMENDED EXAMINATION ITEMS FOR MR. KOIZUMI ARE AS FOLLOWS.

| DISEASE | DISEASE-DEVELOPMENT PROBABILITY | | EXAMINATION | ACCURACY | BALANCE |
|---|---|---|---|---|---|
| DIABETES | 6% | ▼ | BLOOD TEST | B | ¥0 |
| ANGINA PECTORIS | 5% | ▼ | ELECTROCARDIOGRAM | B | ¥0 |
| LARGE-INTESTINE CANCER | 3% | ▼ | STOOL TEST FOR OCCULT BLOOD | C | ¥0 |

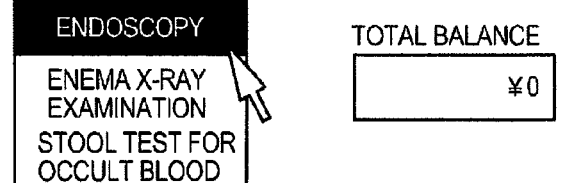

TOTAL BALANCE ¥0

FIG. 14B

RECOMMENDED EXAMINATION ITEMS FOR MR. KOIZUMI ARE AS FOLLOWS.

| DISEASE | DISEASE-DEVELOPMENT PROBABILITY | | EXAMINATION | ACCURACY | BALANCE |
|---|---|---|---|---|---|
| DIABETES | 6% | ▼ | BLOOD TEST | B | ¥0 |
| ANGINA PECTORIS | 5% | ▼ | ELECTROCARDIOGRAM | B | ¥0 |
| LARGE-INTESTINE CANCER | 3% | ▼ | ENDOSCOPY | A | ¥2000 |

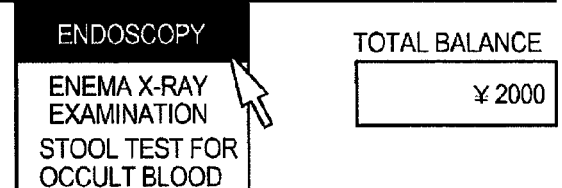

TOTAL BALANCE ¥2000

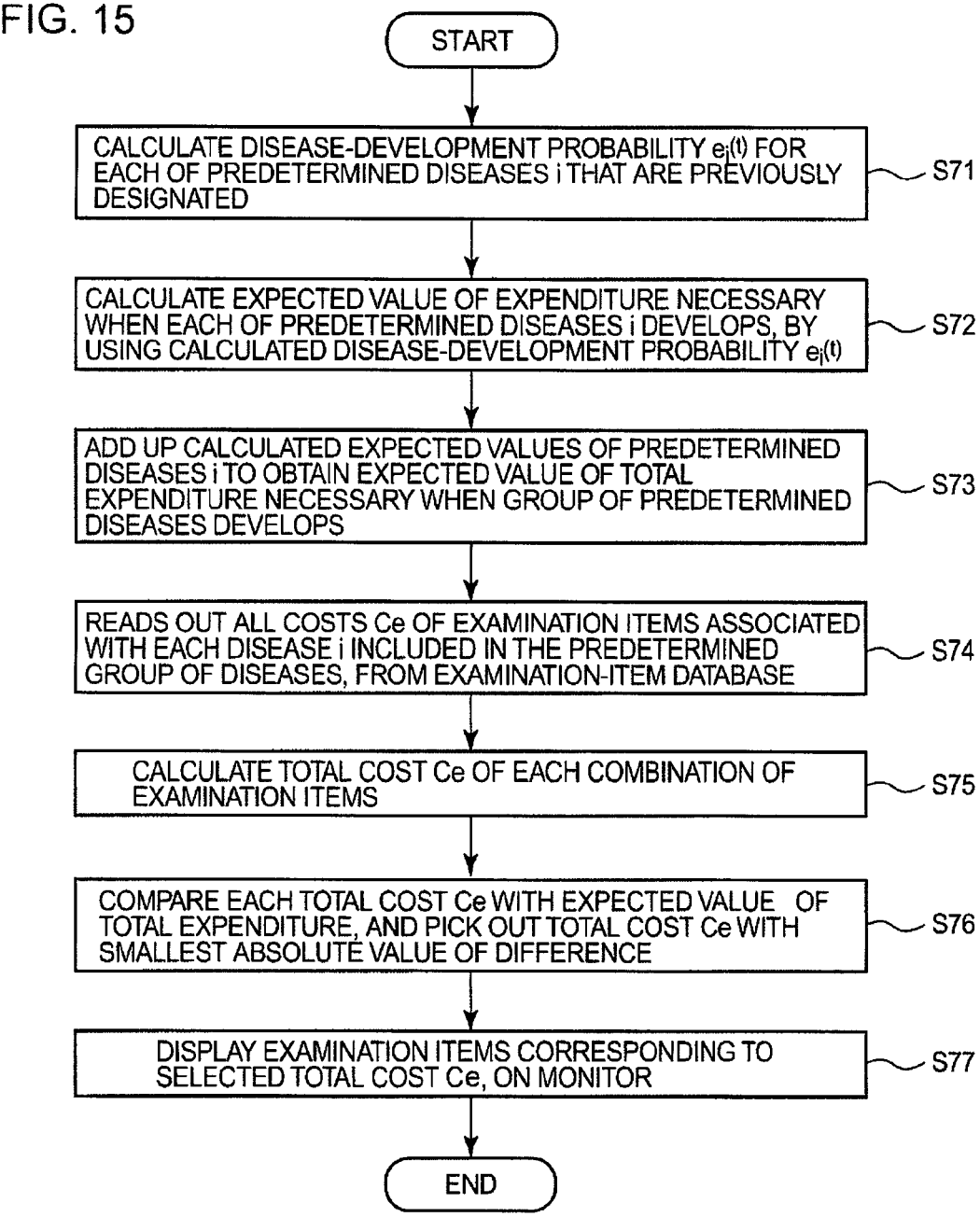

FIG. 16

| DISEASE i | DISEASE-DEVELOPMENT PROBABILITY | EXAMINATION-ITEM | COST |
|---|---|---|---|
| ANGINA PECTORIS | ¥ 12,0000 | EXAMINATION-ITEM A | ¥ 14,000 |
| DIABETES | ¥ 5,000 | EXAMINATION-ITEM B | ¥ 4,000 |
| LARGE-INTESTINE CANCER | ¥ 10,000 | EXAMINATION-ITEM C | ¥ 9,000 |

FIG. 18

| DISEASE | EXAMINATION-ACCURACY RANK C | EXAMINATION-ACCURACY RANK B | EXAMINATION-ACCURACY RANK A |
|---|---|---|---|
| DIABETES | — | BIOCHEMICAL EXAMINATION (DIABETES) | — |
| EXAMINATION COST Ce | — | ¥1500 | — |
| EXAMINATION REFERENCE INFORMATION Fi | | EXAMINATION REFERENCE INFORMATION Fe BIOCHEMICAL EXAMINATION IS······ | |

DISEASE REFERENCE INFORMATION Fi
DIABETES IS······

| DISEASE | EXAMINATION-ACCURACY RANK C | EXAMINATION-ACCURACY RANK B | EXAMINATION-ACCURACY RANK A |
|---|---|---|---|
| COLON CANCER | BIOCHEMICAL EXAMINATION (COLON CANCER) | COLONOSCOPY | ENEMA TISSUE BIOPSY |
| EXAMINATION COST Ce | ¥1500 | ¥9000 | ¥10000 |
| EXAMINATION REFERENCE INFORMATION Fi | EXAMINATION REFERENCE INFORMATION Fe BIOCHEMICAL EXAMINATION IS······ | EXAMINATION REFERENCE INFORMATION Fe COLONOSCOPY IS······ | EXAMINATION REFERENCE INFORMATION Fe ENEMA TISSUE BIOPSY IS······ |

DISEASE REFERENCE INFORMATION Fi
COLON CANCER IS······

FIG. 20

| DISEASE | DISEASE-DEVELOPMENT PROBABILITY | EXAMINATION-ACCURACY RANK C | EXAMINATION-ACCURACY RANK B | EXAMINATION-ACCURACY RANK A |
|---|---|---|---|---|
| DIABETES | 1% | ◯ | ⦿ BIOCHEMICAL EXAMINATION (DIABETES) | ◯ |
| | EXAMINATION COST Ce | — | ¥1500 | — |
| | DISEASE REFERENCE INFORMATION Fi DIABETES IS······ | | EXAMINATION REFERENCE INFORMATION Fe BIOCHEMICAL EXAMINATION IS···· | |

| DISEASE | DISEASE-DEVELOPMENT PROBABILITY | EXAMINATION-ACCURACY RANK C | EXAMINATION-ACCURACY RANK B | EXAMINATION-ACCURACY RANK A |
|---|---|---|---|---|
| COLON CANCER | 0.5% | ⦿ BIOCHEMICAL EXAMINATION (COLON CANCER) | ◯ COLONOSCOPY | ◯ ENEMA TISSUE BIOPSY |
| | EXAMINATION COST Ce | ¥1500 | ¥9000 | ¥10000 |
| | DISEASE REFERENCE INFORMATION Fi COLON CANCER IS······ | EXAMINATION REFERENCE INFORMATION Fe BIOCHEMICAL EXAMINATION IS··· | EXAMINATION REFERENCE INFORMATION Fe COLONOSCOPY IS······ | EXAMINATION REFERENCE INFORMATION Fe ENEMA TISSUE BIOPSY IS····· |

[ SETTLE ]    [ CANCEL ]

EXAMINATION-ITEM-SELECTION DEVICE, AN EXAMINATION-ITEM-SELECTION METHOD, AND AN EXAMINATION-ITEM-SELECTION PROGRAM

BACKGROUND OF THE INVENTION

1. Field of the Invention

The present invention is related to a technique for predicting a disease that one is predisposed to, based on physical information for each individual, and selecting the optimal examination item by taking the results of those predictions into account.

2. Description of the Related Art

With recent rapid development of statistical approaches such as data mining, and enhancement of a variety of data used in the statistical approaches, it has become possible to predict various changes in condition of an individual body. Predictions of future changes in condition are used for medical policy, instructions for maintenance or improvement of health, and the like.

For example, a technique for predicting life expectancy that an individual is expected to live healthily (healthy life expectancy) based on physical information of the individual, and making use of the prediction results for establishment of a health-management plan and prediction of the effects of execution of the health-management plan, is presented (e.g. cf. Japanese Unexamined Patent Application Publication 2003-167959). This technique utilizes physical information on an individual body, such as daily living habits related to smoking, drinking and exercise and diagnostic results of obesity, hyperpiesia, hyperlipemia, hyperglycemia, hyperuricemia and so on. Moreover, based on a certain population having a combination of the physical information, basic data is prepared, in which the probability that an individual having the combination of the physical information can live in a healthy condition is sectionalized for each age. For example, basic data as to what percent for each age group of people who smoke, drink and are obese live in a healthy condition, when age 0 is 100%, is prepared. A predicted value of healthy life expectation is calculated by applying individual physical information to this basic data. Then, the degree of future development of a disease or a disorder is determined based on the predicted value of healthy life expectation, and a plan for setting intervals for performing health diagnoses or the like is created based on the determination result.

Further, for example, a technique for predicting the probability of development of a predetermined disease based on individual physical information, and displaying by color-coding the prediction results along with values of the physical information, is presented (e.g. cf. Japanese Unexamined Patent Application Publication 2005-49921). This technique is to detect the development probability of diabetes in a statistical approach by using physical information such as BMI (Body Mass Index) and blood glucose level, and specify the risk by color-coding the values of the physical information based on the development probability. This color-coded display is made use of when a physician or the like suspects disease development or gives an instruction for lifestyle.

In a current medical examination for detecting a disease, all subjects undergo an examination with the same content without variation to detect a specific disease. For example, the subject generally undergoes an X-ray barium contrast examination without variation for the purpose of detecting stomach cancer. However, predispositions to diseases vary greatly among individuals. Some people are likely to develop a certain disease, but other people are not likely to develop that disease and likely to develop another disease instead. Therefore, in the current situation in which all subjects undergo the same examination without variation for the purpose of detecting the same disease without variation, the optimal examination for an individual is not performed, so that many diseases may be missed. In addition, undergoing an examination that is not necessary to an individual undergoing medical examination results in imposing superfluous physical, psychological and even financial burdens on the individual.

With the technique for predicting healthy life expectancy of an individual based on physical information of the individual, and making use of the prediction result for establishment of a health-management plan and prediction of the effect of execution of the health-management plan, it is possible to conceptualize a certain degree of disease development from the healthy life expectation. However, it is impossible to predict what type of disease will develop, from the conceptualization alone. Therefore, it is impossible to select an examination that the individual should take. Meanwhile, with the technique for predicting the development probability of a predetermined disease based on individual physical information and displaying by color-coding the prediction result and the physical information, it is possible to predict the development probability for each disease. However, it cannot be said that how to handle the prediction result is established. Therefore, the prediction result of the disease development probability remains only a reference. In other words, eventually, the same examination will be taken without variation for the purpose of detecting the same disease without variation.

As stated above, with the conventional techniques, it becomes possible to predict various state changes related to an individual body by using a statistical approach, but it is difficult to select the optimal examination item for each individual. Therefore, it is impossible to solve the current problem that many diseases are missed and superfluous physical, psychological and even financial burdens are imposed on a person undergoing medical examination.

SUMMARY OF THE INVENTION

The present invention has been achieved by considering the above circumstances, and an object of the present invention is to provide a technique for predicting a disease that an individual is predisposed to based on physical information of the individual and selecting the optimal examination item by taking the prediction result into account.

For solving the above problem, in a first aspect of the present invention: an examination-item database storing a plurality of types of examination items capable of examining a predetermined disease and attributes of the examination items so as to correspond to one another is prepared; calculation of a degree of risk for development of the predetermined disease based on individual physical information is performed; generation of a criterion for selection of the examination item for examining the predetermined disease in accordance with the calculated degree of risk is performed; and search of an examination item having an attribute meeting the selection criterion from the examination-item database is performed. According to the first aspect, it is possible to perform the optimal examination for each individual depending on the disease-development probability, thereby improving the efficiency of detection of diseases. Moreover, reduction of superfluous examinations makes it possible to reduce physical and psychological burdens imposed on the subject.

In a second aspect of the present invention: the examination-item database pre-stores examination-accuracy information of an examination corresponding to the examination item, as the attribute of the examination item; in the generation of the selection criterion, a table of the examination-accuracy information divided into cases in accordance with the degree of risk is prepared, and examination-accuracy information divided into cases in accordance with the calculated degree of risk is generated with the table; and in the search, an examination item coupled with the generated examination-accuracy information is searched out from the examination-item database. According to the second aspect, it is possible to perform the optimal examination for each individual from the viewpoint of the degree of the risk versus the examination accuracy, and thus improve the probability of detection of a disease with more efficiency.

In a third aspect of the present invention: the examination-item database pre-stores cost of an examination corresponding to the examination item, as the attributes of the examination item; in the generation of the selection criterion, expenditure information indicating expenditure becoming necessary due to disease development is pre-stored, and an expected value of the expenditure becoming necessary due to the disease development is generated by using the calculated degree of risk and the expenditure information; and in the search, an examination item coupled with the cost below the expected value obtained by a criterion generator is searched out from the examination-item database. According to the third aspect, it is possible to perform the optimal examination for each individual from the viewpoint of the disease-development probability versus the cost, and reduce financial burden.

In a fourth aspect of the present invention: an examination-item database pre-storing a plurality of types of examination items capable of examining the predetermined disease and attributes of the examination items so as to correspond to one another is prepared; the degree of risk for developing the predetermined disease is calculated based on individual physical information; and the calculated degree of risk and the examination-item database are displayed so as to correspond to the predetermined disease. According to the fourth aspect, by presenting a plurality of suggestions of examination items by which a disease can be examined, and displaying both the degree of the risk and the attributes of the examination items, a user can select an examination item to undertake with reference to the degree of the risk and the attributes of the examination item, so that selection of the examination item can be assisted.

In a fifth aspect of the present invention: a method-input part is provided, into which a selection method is adopted and inputted from among various methods for selecting examination items; disease-development probability of a predetermined disease is calculated based on individual physical information; and an examination item for examining the predetermined disease is selected with the inputted selection method. According to the fifth aspect, it is possible to select various selection methods, so that it becomes possible to select an examination item more reflecting the needs of the individual to undergo examination.

BRIEF DESCRIPTION OF THE DRAWINGS

FIG. 2 shows a database of correlation function $f_j(X)$.
FIG. 3 shows a database of correlation function $A_{ij}$.
FIG. 4A and FIG. 4B are diagrams that show physical information of an individual.
FIG. 6 is a pattern diagram that shows a screen that displays calculated disease-development probability.
FIG. 7 is a diagram that shows selection criterion data according to the first embodiment.
FIG. 8 is a diagram that shows an examination-item database according to the first embodiment.
FIG. 9 is a flowchart that shows an operation of selecting an examination item according to the first embodiment.
FIG. 10 is a pattern diagram that shows a screen that displays a list of examination items selected by a searching portion 30 in the first embodiment.
FIG. 11 is a diagram that shows selection criterion data according to a second embodiment.
FIG. 12 is a diagram that shows an examination-item database according to the second embodiment.
FIG. 14 is a diagram that shows a display of selected examination items according to a third embodiment.
FIG. 15 is a flowchart that shows an operation of selecting an examination item according to a fourth embodiment.
FIG. 16 is a diagram that shows a display of the selected examination items according to the fourth embodiment.
FIG. 18 is a diagram that shows an examination-item database according to the fifth embodiment.
FIG. 20 is a diagram that shows a screen on which disease-development probability and examination items for examining a disease are displayed side by side in the fifth embodiment.

DETAILED DESCRIPTION OF THE EMBODIMENTS

Figure 1:
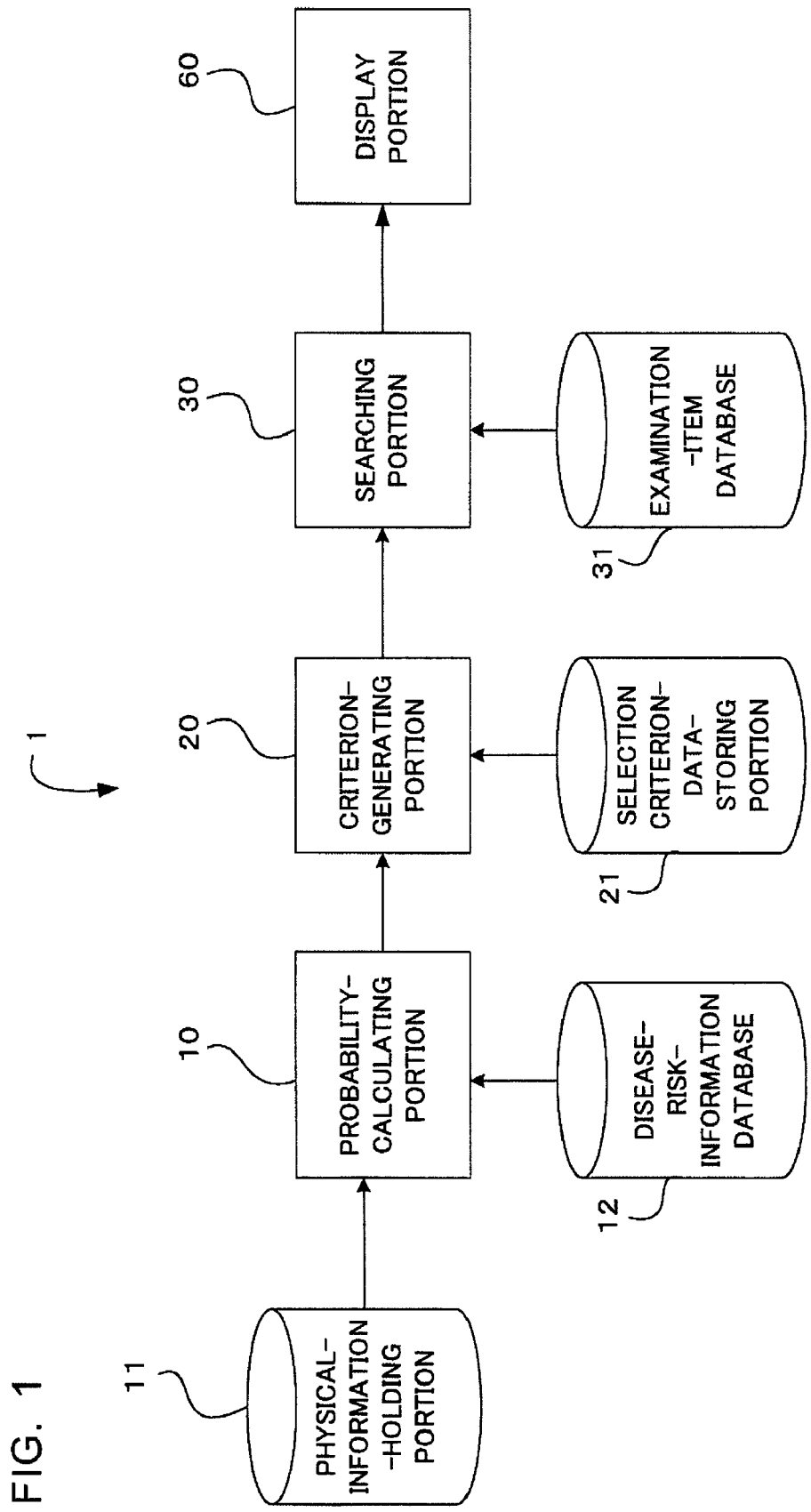
FIG. 1 is a block diagram that shows a configuration of an examination-item-selection device that uses an examination-item-selection method according to a first embodiment.

Hereinafter, a preferred embodiment of examination item selection according to the present invention will be explained in detail referring to the drawings.

First Embodiment

An examination-item-selection method according to a first embodiment is to predict the degree of risk for developing various diseases in a statistical approach based on individual physical information, generate a criterion for selecting examination items according to the predicted degree of risk, and select an examination item that has an attribute satisfying the selection criterion.

The degree of risk for developing a disease is the probability that expresses development of the disease in percentage, or sections such as high, middle and low. The attributes of the examination items to be used in selection of an examination item are, for example, the examination accuracy, the cost of the examination, the dangerousness of the examination, the invasiveness caused by the examination, the reliability of the examination, the examination time, the physical and psychological burdens imposed by the examination, and so on, and they are represented by quantifying or sectionalizing. As the criteria for selection, that of a type in conformity with the attributes of the examination item to be utilized in the selection of an examination item is generated. The disease-development probability is sectionalized depending on the degree thereof, and this section is associated with the numeric value and section of the attribute of the examination item to be utilized in the selection. The numeric value and section of the attribute of the examination item that is associated with the section to which the predicted disease-development probability belongs is used as the criteria for selection. Alternatively, the selection criteria may be generated by using the disease-development probability as a parameter, and used as a target for comparison with the attribute value of the examination item to be utilized in the selection. The examination item that has an attribute satisfying the criteria for selection is then selected.

In the first embodiment, an examination item is selected based on the disease-development probability versus the examination accuracy. In other words, the criteria for selection is the examination accuracy recommended according to the disease-development probability. An examination item that has an examination accuracy meeting the recommended examination accuracy is selected.

This examination-item-selection method is performed by, for example, causing a computer to execute a program for realizing the examination-item-selection method. FIG. 1 is a block diagram that shows a configuration of an examination-item-selection device that specifically implements the examination-item-selection method according to the first embodiment. For example, this examination-item-selection device 1 comprises a computer in which an arithmetic controller (CPU: Central Processing Unit or a graphic chip), a main storing portion (RAM: Random Access Memory) and an external storing portion (HDD: Hard Disk Drive) are connected by a common line and are capable of inputting/outputting data mutually, and comprises a monitor and an input interface. A program for implementing the examination-item-selection method is stored in the external storing portion and the program is executed as needed. The monitor is composed of an LCD (Liquid Crystal Display) or a CRT (Cathode Ray Tube) display. The input interface is a keyboard, a mouse that has a wheel-tracking function, or the like.

By executing the program stored in the external storing portion, the examination-item-selection device 1 comprises a probability-calculating portion 10, a physical-information-holding portion 11, a disease-risk-information database 12, a criterion-generating portion 20, a selection criterion-data-storing portion 21, a searching portion 30, an examination-item database 31, and a display portion 60. The probability-calculating portion 10, the physical-information-holding portion 11 and the disease-risk-information database 12 are configurations for calculating the disease-development probability. The criterion-generating portion 20 and the selection criterion-data-storing portion 21 are configurations for generating the criteria of selection. The searching portion 30 and the examination-item database 31 are a configuration for selecting an examination item based on the criteria of selection. The display portion 60 is a monitor, and displays the selected examination item.

First, the calculation of the disease-development probability as the degree of risk for developing a disease is explained. In the present embodiment, a development-risk-calculating part for calculating the degree of risk of developing a disease is the probability-calculating portion 10. The probability-calculating portion 10 calculates the disease-development probability for an individual within the next predetermined period, by using physical information and disease-risk information. The physical information is diagnostic information such as blood pressure that has been obtained by health diagnoses or the like and gene information that has been obtained by gene analysis. The disease-risk information is a normalization function for converting the physical information into a variable that specifies what distribution of the disease-development probability it belongs to and a correlation coefficient that indicates a correlation between the variable obtained by the normalization and the disease development. The probability-calculating portion 10 performs normalization to the physical information to indicate which distribution of the disease-development probability it belongs to. Furthermore, the probability-calculating portion 10 compensates with the correlation coefficient that indicates the correlation between the normalized physical information and the disease development. As a result, the disease-development probability obtained from one of the pieces of physical information will be found. Furthermore, the total disease-development probability is found by adding up the disease-development probabilities obtained from each piece of physical information. In other words, the probability-calculating portion 10 computes the disease-development probability using the following calculating formulae:

$$e_i = A_{i0} + \sum_{j}^{N} A_{ij} f_j \qquad \text{Mathematical Formula 1}$$

$$e_i^{(t)} = 1 - (1 - e_i)^{(t)} \qquad \text{Mathematical Formula 2}$$

Reference symbol 'e' denotes the disease-development probability of the disease i within the next one year based on the physical information j. Reference symbol '$e^{(t)}$' denotes the disease-development probability of the disease i within the next t years based on the physical information j. Reference symbol '$f_j$' denotes the variable obtained by normalizing the value X of the physical information j with the normalization function $f_j(X)$. Reference symbol '$A_{ij}$' denotes the correlation coefficient that indicates the correlation between the variable obtained by normalizing the value X of the physical information j on the disease i with the normalization function $f_j(X)$ and the disease development. Reference symbol '$A_{i0}$' denotes the fundamental probability that the disease i will develop for anyone regardless of the value X of individual physical information j.

The probability-calculating portion 10 calculates the disease-development probability for the next t years by applying the value X of the physical information j, the normalization function $f_j(X)$, the correlation coefficient $A_{ij}$ and the number of years t to the above calculation formulae. The number of years t is pre-stored in the external storing portion. For example: when t=3 is stored, the disease-development probability for the next three years is calculated by reading out t=3; and when t=5 is stored, the disease-development probability for the next five years is calculated by reading out t=5. The number of years t may be set for each disease i, or a uniform number of years may be set regardless of the type of the disease i. Data having been inputted by using the input interface is stored as the number of years t. For example, additions or modifications can be performed when new knowledge is obtained as to what number of years t of the disease i the disease-development probability is most actual.

The value X of various physical information j is stored in the physical-information-holding portion 11. The probability-calculating portion 10 reads, from the physical-information-holding portion 11, the value X of the physical information j relating to the development of the disease i for which the disease-development probability is to be calculated.

The normalization function $f_j(X)$ and the correlation coefficient $A_{ij}$ are stored in the disease-risk-information database 12. Among the normalization functions $f_j(X)$ and the correlation coefficients $A_{ij}$ that are stored in the disease-risk-information database 12, the normalization function $f_j(X)$ and the correlation coefficient $A_{ij}$ that are necessary to calculate the disease-development probability based on the value X of the physical information j is read out.

FIGS. 2 and 3 show the disease-risk-information database 12. FIG. 2 shows a database of the normalization function $f_j(X)$. As shown in FIG. 2, the disease-risk-information database 12 stores information on the type of the physical information j used in calculation of the disease-development probability, information on the type of the normalization function $f_j(X)$ for normalizing the value X of the individual physical information j corresponding to the type of the physical information j, and an execution file of the normalization function $f_j(X)$ in a state associated with each other.

The type information of the physical information j stored in the disease-risk-information database 12 is type information of the physical information j considered to relate to disease development from known knowledge. The type information of the physical information j is stored with symbol or name, such as "j=1, 2, 3 . . . " or "angiotensin converting enzyme (ACE) alter, blood glucose level, total cholesterol . . . ." The type information of the normalization function $f_j(X)$ stored in the disease-risk-information database 12 is type information of the normalization function $f_j(X)$ that best represents which distribution of the disease-development probability the physical information j belongs to from known knowledge. The type information of the normalization function $f_j(X)$ is stored with symbol or name, such as "$f_1(X), f_2(X), f_3(X) \ldots$" or "binary, step function, sigmoid function . . . " The execution file of the normalization function $f_j(X)$ can be directly described in the disease-risk-information database 12. Alternatively, a storing-destination pass, such as a directory in which the execution file of the normalization function $f_j(X)$ is stored, may be stored in the disease-risk-information database 12. The type information of the physical information j, the type information of the normalization function $f_j(X)$, and the execution file are inputted by using the input interface, and stored in the disease-risk-information database 12. For example, an addition or a modification may be performed when new knowledge is obtained.

The disease-risk-information database 12 stores, for example, the type information of a binary function "$f_1(X)$" for normalizing the presence or absence of the angiotensin converting enzyme (ACE) alters into either digit of the binary, with respect to the type information "j=1" of the angiotensin converting enzyme alter. The type information of the normalization function is stored, including an offset value and a scale value. The type information of the step function "$f_2(X)$" is stored with respect to the type information "j=2" of the blood glucose level. The type information of the normalization function includes an offset value and a scale value. The type information of the sigmoid function "$f_3(X)$" is stored with respect to the type information "j=3" of the total cholesterol value. The type information of the normalization function is stored, including an offset value and a scale value. The type information of the linear function $f_4(X)$ is stored with respect to the type information "j=4" of the smoking history. The type information of the normalization function is stored, including an offset value and a scale value. The type information of the exponential function "$f_5(X)$" is stored in pairs with respect to the type information "j=5" of the blood pressure value. The type information of the normalization function is stored, including an offset value and a scale value. The type information of the function $f_6(X)$ for finding the product of a value obtained by normalizing the blood glucose level with the step function and a value obtained by normalizing the blood pressure value with the exponential function, is stored with respect to the type information "j=6" of the product of the normalized blood pressure value and blood glucose level. In addition, the type information of the function "$f_7(X)$" for finding the logical product of a value obtained by the binary function for normalizing the presence or absence of the angiotensin-converting enzyme (ACE) alters into either digit of the binary and a value obtained by normalizing the blood pressure value with the exponential function, is stored with respect to the type information "j=7" of the logical product of the angiotensin-converting enzyme alter and the blood glucose level.

The probability-calculating portion 10 reads out from the physical-information-holding portion 11, with sequential reference to the type information of the physical information j (j=1, 2, 3 . . . ), the value X of the physical information j identified by this type information. In addition, the probability-calculating portion 10 selects the normalization function $f_j(X)$ to be executed, with reference to the type information of the normalization function $f_j(X)$ corresponding to the type information of the physical information j having been referred to. The probability-calculating portion 10 reads out the file associated with the normalization function $f_j(X)$ to be executed, and executes normalization of the value X of the physical information j read out from the physical-information-holding portion 11.

FIG. 3 shows a database of the correlation coefficient $A_{ij}$. As shown in FIG. 3, the disease-risk-information database 12 stores, for each combination of a variable $f_j$ and a disease i, the correlation coefficient $A_{ij}$ for compensating the variable $f_j$ of the physical information j obtained by normalization. As this correlation coefficient $A_{ij}$, a coefficient that best represents the correlation between the variable $f_j$ obtained by normalization and the disease development is prepared from known knowledge. The correlation coefficient $A_{ij}$ inputted by using the input interface is stored in the disease-risk-information database 12. For example, additions or modifications can be performed when new knowledge is obtained. Upon calculating each variable $f_j$ (j=1, 2, 3 . . . ), the probability-calculating portion 10 sequentially reads out, from the disease-risk-information database 12, the correlation coefficient $A_{ij}$ for each combination of the disease i and the variable $f_j$, compensates the variable $f_j$ with $A_{ij}$, and sequentially calculates the disease-development probability of various diseases i to one piece of physical information j. The probability-calculating portion then adds up the disease-development probabilities of diseases i to various types of physical information j to ultimately find the comprehensive disease-development probability.

FIG. 4 and FIG. 4B are diagrams that show individual physical information j stored in the physical-information-holding portion 11. As a matter of convenience, FIG. 4 is divided into two figures, however, the diagrams shown in FIG. 4A and FIG. 4B may be configured as one database. As shown in FIG. 4A and FIG. 4B, the physical-information-holding portion 11 stores various kinds of individual physical information j that are quantified or symbolized to represent the presence or absence. This individual physical information j is composed of diagnostic information and gene information. The diagnostic information is either an electronic chart or a database compiled with information extracted from an electronic chart. The value X of the physical information j is ultimately represented with numeric values. For example, the presence or absence of the angiotensin-converting enzyme alter is represented with binary numeric values: "1" if present and "0" if absent. When there is a medical history of appendicitis, the elapsed years, the presence or absence of surgery, the presence or absence of a complete recovery, any medical agents that were administered, the administered dose of the medical agents, the elapsed years after administration of the medical agents, and so on, are quantified. As for the gene information, a database is compiled with the name of the gene responsible for the disease i that an individual has or, when the gene is a multiple-classification type, the name up until the multiple-class; this will be replaced with a symbol like "1" to indicate the presence of the gene in the previous stage of calculation of the disease-development probability. In specific, for each physical information j described in the electronic chart, the value X thereof is stored in the physical-information-holding portion 11. The physical information j described in the electronic chart is: physical numeric values of an individual like the age, sex, body height, body weight, systolic blood pressure, diastolic blood pressure, degree of obesity, BMI (Body Mass Index), body fat percentage, visual acuity, protein, sugar, occult blood, white-blood-cell count, red-blood-cell count, hemoglobin content, hematocrit, GOT, GPT, γ-GTP, AL-P, total cholesterol, neutral fat, HDL cholesterol, uric acid, creatinine, blood glucose and HbA1c; medical histories of appendicitis, right ankle sprain, cholelithiasis, the presence or absence of allergies and so on; and various kinds of blood-biochemical examinations.

This diagnostic information is stored into the physical-information-holding portion 11 by, for example, reading the electronic chart (Karte), or inputting an item desired to be extracted with the input interface. In a case where there is a tag defined for each item by format standardization of the electronic chart, and the corresponding diagnostic information is described after the tag, a tag of a necessary item is found from the electronic chart to obtain necessary diagnostic information. The electronic chart may be obtained from the HIS (Hospital Information System) through a network in the hospital. In this case, the examination-item-selection device 1 has a LAN interface and is communicably connected to the network in the hospital. As a specific example of the gene information, when an individual has the "CYP1A1" gene and "GST1" gene, which are considered to be responsible for development of lung cancer, the name of the gene and the classifications "A-type," "B-type," or "C-type," or "plus-type" or "minus-type," are stored. In a case where all gene names of an individual are stored as gene sequences, the gene information responsible for the disease of the individual is extracted by screening with a known gene name and classification responsible for the disease i or the gene sequence. Therefore, a database for known genes responsible for the disease i may be provided separately from the physical-information-holding portion 11.

The probability-calculating portion 10 reads out the type information of the physical information j stored in the disease-risk-information database 12, and obtains the value X of the physical information j corresponding to this type information, from the physical-information-holding portion 11.

Figure 5:
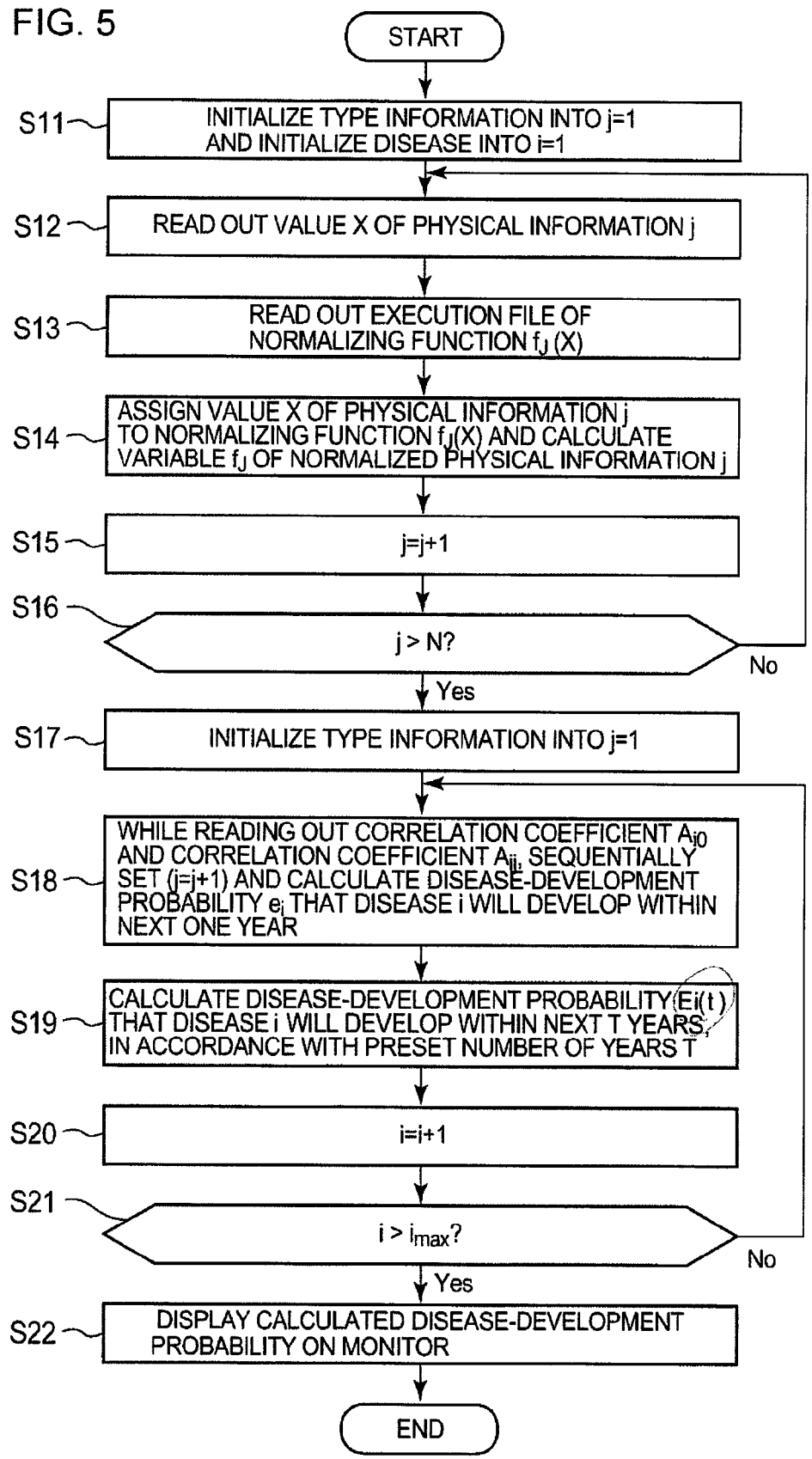
FIG. 5 is a flowchart that shows an operation of calculating disease-development probability.

FIG. 5 is a flowchart that shows the operation for calculating the disease-development probability undertaken by this probability-calculating portion 10. First, the probability-calculating portion 10 initializes the type information of the physical information j into j=1 and initializes the type of the disease i into i=1 (S11). After the initialization, the probability-calculating portion 10 reads out the value X of the physical information j from the physical-information-holding portion 11 (S12). Furthermore, the probability-calculating portion 10 refers to the type information of the normalizing function $f_j(X)$ corresponding to the physical information j in the disease-risk-information database 12, and reads out an execution file of the normalizing function $f_j(X)$ that is associated with this type information (S13).

After reading out the data, the probability-calculating portion 10 assigns the value X of the physical information j to the normalizing function $f_j(X)$ and calculates the variable $f_j$ of the normalized physical information j (S14). After normalizing the value X of the physical information j, the probability-calculating portion 10 sets j=j+1 (S15). When determining not j>N (S16, No), the probability-calculating portion 10 repeats S12 through S15, and normalizes each piece of the physical information j. Here, N denotes the number of pieces of physical information j to be used in the calculation of the disease-development probability. N varies along with modification of or addition to the physical-information-holding portion 11 or the disease-development-risk-information database 12, and is updated and stored by the probability-calculating portion 10 by fixing the modification or addition. If j>N (S16, Yes), the probability-calculating portion 10 initializes into j=1 (S17). Then, the probability-calculating portion 10, while reading out the correlation coefficient $A_{i0}$ and the correlation coefficient $A_{ij}$ from the disease-risk-information database 12, sequentially sets (j=j+1), and calculates the disease-development probability $e_i$ that the disease i will develop within the next one year (S18). After calculating the probability $e_i$, the probability-calculating portion 10 calculates the disease-development probability $e_i^{(t)}$ that the disease i will develop within the next t years, in accordance with the preset number of years t (S19).

After calculating the disease-development probability $e_i^{(t)}$, the probability-calculating portion 10 sets i=i+1 (S20). If not i>$i_{max}$ (S21, No), the probability-calculating portion 10 calculates the disease-development probability $e_i^{(t)}$ for the next t years of each disease i (i=1, 2, 3 . . . ) by repeating S18 and S20. Here, $i_{max}$ denotes the number of diseases i for which the disease-development probability is to be calculated. The $i_{max}$ varies along with modifications of or additions to the disease-development-risk-information database 12, and is updated and stored by the probability-calculating portion 10 by fixing the modifications or additions. When i>$i_{max}$ (S21, Yes) and the disease-development probability $e_i^{(t)}$ is calculated for all diseases i, the probability-calculating portion 10 displays the calculated disease-development probability on the monitor (S22) and ends the process.

FIG. 6 is a pattern diagram that shows a screen displaying the calculated disease-development probability. After calculating the disease-development probability, the probability-calculating portion 10 displays the disease-development probability on the monitor. The disease-development probability of the disease i and the name of the disease i are displayed in pairs on the display screen.

Next, selection of an examination item according to the disease-development probability is explained. In the selection of an examination item, the criterion-generating portion 20 generates the examination accuracy according to the disease-development probability as criteria for selection, and the searching portion 30 searches an examination item that has the examination accuracy satisfying the selection criterion of the examination accuracy.

The criterion-generating portion 20 generates examination-accuracy information depending on the degree of the calculated disease-development probability, by using the selection criterion data. The examination-accuracy information is information that represents by rank the probability of detection of a disease by an examination, and is selection-criterion information that is sectionalized according to rank. The selection criterion data is stored in the selection criterion-data-storing portion 21. FIG. 7 shows the selection criterion data according to the first embodiment. The selection criterion data is a table that stores a section Div in which the disease-development probability is divided into cases for each disease i, and an examination-accuracy rank R corresponding to this section Div. The section Div of the disease-development probability is stored for each number of years t for which the disease-development probability is calculated. For example, when the disease i is "colon cancer," it is divided into three sections Div: "the disease-development probability within the next three years is 3% or more," "the disease-development probability within the next three years is 1% or more and less than 3% or the disease-development probability within the next five years is 1.5% or more," and "the disease-development probability within the next three years is 0.5% or more and less than 1%." Furthermore, as the examination-accuracy rank R, "rank A" is made to correspond to the section Div "the disease-development probability within the next three years is 3% or more," "rank B" is made to correspond to the section Div "the disease-development probability within the next three years is 1% or more and less than 3% or the disease-development probability within the next five years is 1.5% or more," and "rank C" is made to correspond to the section Div "the disease-development probability within the next three years is 0.5% or more and less than 1%." The earlier in the alphabet the rank indicated in the examination-accuracy rank R comes, the higher the examination accuracy is. The criterion-generating portion 20 reads out the selection criterion data for the disease i, searches the Div that includes the calculated disease-development probability, and obtains the examination-accuracy rank R corresponding to this section Div. When there is no section Div that includes the calculated disease-development probability, the examination-accuracy rank R is not obtained. This is because the disease-development probability is low and hence it is not necessary to select an examination item.

The searching portion 30 selects an examination item by searching from the examination-item database 31 the examination-accuracy rank R obtained by the criterion-generating portion 20. An examination item that has an examination-accuracy rank R identical to the selection-criterion information obtained by the criterion-generating portion 20 (the obtained examination-accuracy rank R) is found from the examination items related to the disease i. FIG. 8 shows the examination-item database 31 that is searched by the searching portion 30. The examination-item database 31 stores, for each disease i, various examination items that can examine the disease i, and further sectionalizes each examination item according to the examination-accuracy rank R. For example, a biochemical examination (colon cancer marker), a colonoscopy, and a large-intestine-tissue biopsy are stored as examination items for colon cancer. The biochemical examination (colon cancer marker) is sectionalized into the rank C, the colonoscopy is sectionalized into the rank B, and the large-intestine-tissue biopsy is sectionalized into the rank A. With reference to the examination-item database 31 of the disease i for which the examination-accuracy rank R has been obtained, the searching portion 30 picks out the examination item that is sectionalized into the obtained examination-accuracy rank R.

FIG. 9 is a flowchart that shows the operation for selecting an examination item by this criterion-generating portion 20 and searching portion 30 according to the first embodiment. First, the criterion-generating portion 20 initializes the type of the disease i into i=1 (S31). After the initialization, the criterion-generating portion 20 reads out the disease-development probability $e_i^{(t)}$ of the disease i within the next t years calculated by the probability-calculating portion 10 (S32), and then reads out the selection criterion data of the disease i from the selection criterion-data-storing portion 21 (S33). After reading out the disease-development probability $e_i^{(t)}$ of the disease i within the next t years and the selection criterion data of the disease i, the criterion-generating portion 20 applies the disease-development probability $e_i^{(t)}$ to the section Div in which the disease-development probability corresponding to the number of years t in the selection criterion data is divided into cases, and searches for a conforming section Div (S34).

Upon finding the conforming section Div (S34, Yes), the criterion-generating portion 20 refers to the examination-accuracy rank R corresponding to the conforming section Div in the selection criterion data, and associates it with the disease i to generate the identical examination-accuracy rank R (S35). When not finding the conforming section Div (S34, No), the criterion-generating portion 20 ends obtaining the examination-accuracy rank R for the disease 1, without obtaining the examination-accuracy rank R. After ending the search, the criterion-generating portion 20 sets i=i+1 (S36). If not i>$i_{max}$ (S37, No), the criterion-generating portion 20 repeats S32 through S36 to generate the examination-accuracy rank R associated with each disease i.

When i>$i_{max}$ (S37, Yes) and the examination-accuracy rank R that has been associated with each disease i is generated by the criterion-generating portion 20, the searching portion 30 initializes into i=1 (S38) and reads the examination-item database 31 (S39). The searching portion 30 searches for the items of the disease i from the read examination-item database 31 (S40), and further searches for the examination item in which the examination-accuracy rank R is associated with the disease i from the examination items associated with the searched disease i (S41). When the examination item is found, the searching portion 30 sets i=i+1 (S42). If not 1>$i_{max}$ (S43, No), the searching portion 30 repeats S39 through S42 to search, for each disease i, the examination item having an examination-accuracy rank R identical to the selection-criterion information. When i>$i_{max}$ (S43, Yes) and examination items for all diseases i are found, the searching portion 30 displays, on the monitor, each disease i and the examination items of the diseases i that have been searched for in combination with one other (S44), and ends the process.

FIG. 10 is a pattern diagram that shows a screen displaying a list of examination items picked out by the searching portion 30 in the first embodiment. Upon picking out the examination items, the searching portion 30 displays a list thereof on the monitor. The examination items picked out for the respective diseases i are displayed on the monitor. The display screen that displays the list of the examination items may display alongside the screen displaying the disease-development probability shown in FIG. 6. In the case of display together, the disease-development probability and the picked-out examination item are displayed side-by-side for each disease i.

In this way, the examination-item-selection device 1 according to the present embodiment calculates the disease-development probability in a statistical approach by using the disease-risk information (normalization function $f_j$ (X) and correlation coefficient $A_{ij}$) from the physical information j, converts the calculated disease-development probability into the examination-accuracy rank R by using the selection criterion data, and selects the examination item having an evaluation meeting the examination-accuracy rank R. This makes it possible to perform the optimal examination for each individual from the viewpoint of the disease-development probability versus the examination accuracy, detect a disease efficiently at an early date, and reduce burdens imposed on a patient by examinations as a result of reduction of superfluous examinations.

Incidentally, the examination accuracy is sectionalized into ranks in the present embodiment, but when the examination accuracy of an examination is replaced with a specific numeric value, the examination item may also be searched for with the numeric value. The minimal examination accuracy recommended depending on the degree of the disease-development probability is stored in the selection criterion data. The searching portion 30 picks out, as the recommended examination items, examination items having a value that either meets or exceeds the minimal examination accuracy. When a plurality of examination items that have the examination accuracy satisfying the minimal examination accuracy are picked out as a result of the search by the searching portion 30, the examination item having the lowest examination accuracy is selected from among the plurality of picked-out examination items. Alternatively, the plurality of picked-out examination items are displayed in its entirety.

The displayed examination items may be associated with the disease-development probability, reference information of the disease i or reference information of examination item, and displayed together. The reference information of the disease i is a string indicating, for example, a risk regarding recovery when the disease i develops, the const of treatment, and a possibility that the quality of life may decrease even after recovery. In addition, the reference information of the examination item is a string that indicates the examination-accuracy rank, the risk for the examination, the cost of the examination, and so on. The reference information of the disease i or the reference information of the examination item can be stored in the examination-item database, in a state associated with each disease i and the examination item (cf. FIG. 18). When displaying the examination item searched from the examination-item database, the searching portion 30 obtains the relevant reference information from the examination-item database, and displays them simultaneously.

In addition, it is sufficient for the physical-information-holding portion 11 to store the latest physical information of an individual, but it is also possible to store information of a plurality of years. In this case, the probability-calculating portion 10 may calculate the disease-development probability of each year, and display on the monitor. This makes it possible to see increase and decrease of the disease-development probability, and is also helpful for guidance to improve one's lifestyle.

Second Embodiment

The examination-item-selection device 1 according to a second embodiment of the present invention is explained. This examination-item-selection device 1 is the same as that of the first embodiment in the configuration for calculating the disease-development probability in a statistical approach by using the disease-risk information from the physical information, generating the selection-criterion information according to the disease-development probability by using the selection criterion data, and selecting an examination item having an attribute satisfying the selection-criterion information. The examination-item-selection device 1 according to the present embodiment materializes a physical-information-holding portion 11, a disease-risk-information database 12 and a probability-calculating portion 10 in order to calculate the disease-development probability by executing a program. In addition, the device comprises a selection criterion-data-storing portion 21, a criterion-generating portion 20, an examination-item database 31 and a searching portion 30 in order to select an examination item.

In the second embodiment, the examination-item-selection device 1 selects an examination item on the basis of treatment costs versus examination costs. In other words, the criterion for selection is an expected value of the expenditure necessary due to the disease development. The attribute of the examination item is the cost for the examination. An examination item having a cost satisfying this expected value is selected.

FIG. 11 shows selection criterion data stored in the selection criterion-data-storing portion 21 of the examination-item-selection device 1 according to the present embodiment. The selection criterion-data-storing portion 21 stores, for each disease i, expenditure information Ct indicating the expenditure when the disease i develops. This expenditure information Ct is treatment cost required for treatment of the disease i. The information is found from the NHI (National Health Insurance) points for a typical therapy performed on a certain disease i, the expense actually incurred when the disease developed in a certain hospital or the accumulation of past statistical data, and is stored in the selection criterion-data-storing portion 21 through the input interface. This expenditure information Ct may include, not only the treatment cost, but also other miscellaneous expenditures for covering the declines in the quality of life caused by treatment (e.g. the cost of a wheelchair, the maintenance expenses for a pacemaker, the cost for conversion to a private car for disabled persons, the cost for conversion to a barrier-free house, and the like). Moreover, the expenditure information Ct may include, not only the treatment cost, but also the cost for damage involved in a risk caused by the examination, such as a medical accident.

The criterion-generating portion 20 reads out the expenditure information Ct for when the disease i develops, from the selection criterion data stored in the selection criterion-data-storing portion 21, and calculates the expected value of the expenses to be paid when the disease i develops, from the read-out expenditure information Ct and the disease-development probability calculated by the probability-calculating portion 10. In other words, the expected value is calculated by multiplying the expenditure indicated in the expenditure information Ct by the disease-development probability. The searching portion 30 searches for an examination with a value of cost below the expected value calculated by the criterion-generating portion 20, from the examination-item database 31, and sets the search result as the examination item having been picked out.

FIG. 12 is a diagram that shows the examination-item database 31 according to the present embodiment. The examination-item database 31 stores, for each disease i, an examination item to examine the disease i, and further stores cost Ce incurred for an examination of the examination item and the examination-accuracy rank R in a state associated with one other. For example, a biochemical examination (colon cancer marker), a colonoscopy, and a large-intestine-tissue biopsy are stored as examination items for colon cancer. The biochemical examination (colon cancer marker) is associated with the cost "1,500 yen" and "rank C," the colonoscopy is associated with the cost "9,000 yen" and "rank B," and the large-intestine-tissue biopsy is associated with the cost "10,000 yen" and "rank A." With reference to the examination-item database 31 of the disease i for which an expected value has been obtained, the searching portion 30 sequentially compares the stored cost Ce associated with each disease item with the expected value. As a result of the comparison, an examination item associated with a cost Ce that is below the expected value is picked out. When a plurality of examination items have cost Ce that is below the expected value, the examination item with the highest examination-accuracy rank R is picked out.

Figure 13:
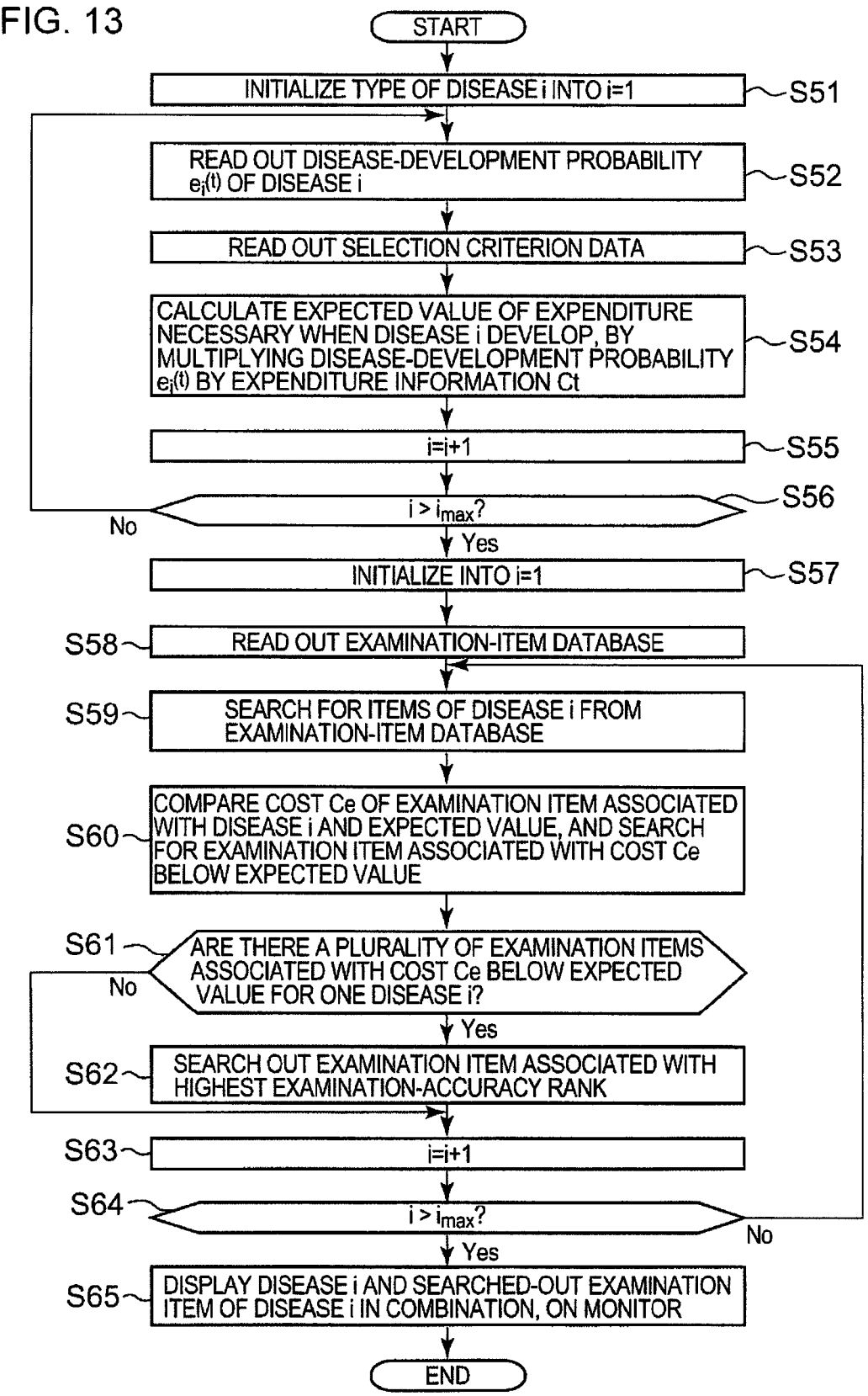
FIG. 13 is a flowchart that shows an operation of selecting an examination item in the second embodiment.

FIG. 13 is a flowchart that shows the operation for selecting an examination item by the criterion-generating portion 20 and the searching portion 30 in the second embodiment. First, the criterion-generating portion 20 initializes the type of the disease i into i=1 (S51). After the initialization, the criterion-generating portion 20 reads out the disease-development probability $e_i^{(t)}$ of the disease i calculated by the probability-calculating portion 10 (S52), and then reads out the selection criterion data of the disease i from the selection criterion-data-storing portion 21 (S53). After reading out the disease-development probability $e_i^{(t)}$ of the disease i and the selection criterion data of the disease i, the criterion-generating portion 20 calculates an expected value of the expenditure that is necessary when the disease i develops, by multiplying the disease-development probability $e_i^{(t)}$ by the expenditure information Ct that is necessary when the disease i develops in the selection criterion-data-storing portion (S54).

Upon calculating the expected value, the criterion-generating portion 20 sets i=i+1 (S55). If not i>$i_{max}$ (S56, No), the criterion-generating portion 20 repeats S52 through S55 to calculate an expected value of the expenditure that is necessary when the disease i develops. When i>$i_{max}$ (S56, Yes) and the expected value of the expenditure that is necessary when the disease i develops is calculated by the criterion-generating portion 20, the searching portion 30 initializes into i=1 (S57) and reads the examination-item database 31 (S58). The searching portion 30 searches for the items of the disease i from the read examination-item database 31 (S59), compares the cost Ce of the examination item associated with the searched disease i and the expected value, and searches for the examination item associated with the cost Ce that is below the expected value (S60). When a plurality of examination items associated with the cost Ce below the expected value exist for one disease i (S61, Yes), the examination item associated with the highest examination-accuracy rank R is searched out (S62).

When the examination item is searched out, the search portion sets i=i+1 (S63). If not i>$i_{max}$ (S64, No), the search portion repeats S59 through S62 to search for the examination item associated with the cost Ce below the expected value and having the highest examination-accuracy rank R, for each disease i. When i>$i_{max}$ (S64, Yes) and examination items for all diseases i are searched out, the searching portion 30 displays, on the monitor, each disease i and the searched-out examination item of the disease i in combination with one other (S65), and ends the process.

In this way, the examination-item-selection device 1 according to the present embodiment calculates the disease-development probability in a statistical approach by using the disease-risk information from the physical information, converts the calculated disease-development probability into the expected value of the expenditure required when the disease develops by using the selection criterion data, and selects an examination item that has a cost below the expected value. This makes it possible to perform the optimal examination for each individual from the viewpoint of disease-development probability versus cost, and reduce both physical and financial burdens imposed on a patient by examinations as a result of reduction of superfluous examinations.

It is also possible to calculate the expected value in a rigorous manner by including, in the calculation, the expense required for treatment of a disease that has been missed in an examination but has developed afterwards, the expense to be incurred for performing early treatment or preventive treatment when judged to be "positive" in an examination, and the cost of an examination. In this calculation of the expected costs, the criterion-generating portion 20 calculates the expected value by computing the following calculating formula:

Expected value=(1−Presence or absence of implementation of examination k)×(Treatment cost required for treatment of disease i)×(Disease-development probability) +(Presence or absence of implementation of examination k)×(Treatment cost required for treatment of disease i)×(Disease-development probability)×(1−Examination accuracy) +(Presence or absence of implementation of examination k)×(Treatment cost required for initial treatment of disease)×(Examination-positive probability) +(Presence or absence of implementation of examination k)×(Cost of Examination k)

"The presence or absence of implementation of examination" is "1" when it is performed, and "0" when it is not performed. "The examination accuracy" is the probability of detection of a disease by a certain examination k. "The examination-positive probability" is the probability of a positive determination in an examination. In the first line of the formula, the expected value of the expense required when the disease i develops in a case where the examination k has not been performed is calculated. In the second line of the formula, the expected value of the expense required for treatment of a disease having been missed in the examination but has developed in a case where the examination K has been performed is calculated. In the third line of the formula, the expense incurred for performing early treatment or preventive treatment when judged to be "positive" in an examination is calculated. In the fourth line of the formula, the cost of performing the examination K is calculated.

The criterion-generating portion 20 computes the above calculation formula for each examination (K=0, 1, 2, . . . ) and each disease i, and by dividing cases between those in which the examination k has been performed and in which the examination k has not been performed, and decides, among the calculated expected values, the minimum one as the ultimate expected value. In order to decide the minimum expected value, a known method such as the simulated annealing method can be employed.

In addition, when a plurality of examination items are picked out, the plurality of examination items may be displayed all on the monitor. Each of the displayed examination items may be associated with the disease-development probability, reference information of the disease i and reference information of each examination item, and displayed simultaneously. The reference information of the disease i or the reference information of each examination item may be stored in the examination-item database by associating them with each disease i and each examination item (cf. FIG. 18). When displaying the examination item searched out from the examination-item database, the searching portion 30 obtains the relevant reference information from the examination-item database and displays them simultaneously on the monitor.

Third Embodiment

In a third embodiment of the present invention, the searching portion 30 compares the cost Ce of each examination item associated with the searched-out disease i and the expected value, picks out the examination item that is associated with the cost Ce below the expected value and associated with the highest examination-accuracy rank R, and displays the examination item on the initial screen, where it is possible to switch the display to another examination item associated with the disease i by using the input interface.

FIG. 14 is a diagram that represents the examination-item-selection result displayed in the present embodiment. In the initial state, as shown in FIG. 14A, the searching portion 30 displays, on the monitor, the disease i, the disease-development probability of the disease i, the searched-out examination item associated with the highest examination-accuracy rank R, and the examination-accuracy rank R, in combination. The searching portion 30 displays, in a section of the displayed examination item, a button for displaying a pull-down menu. When the button is pressed down with the input interface, the searching portion 30 reads out another examination item associated with the disease i, from the examination-item database 31, and displays the item in the pull-down menu. When an examination item other than the currently displayed examination item is chosen with the input interface, the searching portion 30, as shown in FIG. 14B, re-displays the chosen examination item in combination with the corresponding disease i, and further reads out the examination-accuracy rank R of the chosen examination item, from the examination-item database 31, and displays in combination with one other.

For example, in the examination-item database 31, large-intestine cancer is associated with a stool test for occult blood, an endoscopy and an enema X-ray examination. As a result of the selection of the examination item on the basis of the treatment cost versus the examination cost according to the second embodiment, for example, in the initial state, the disease-development probability "3%", the recommended examination item "stool test for occult blood", and the examination-accuracy rank R "C" are displayed in combination. When the button displayed near the section of the examination item is pressed down, the searching portion 30 displays a pull-down menu and displays, in the pull-down menu, all the examination items associated with large-intestine cancer (i.e. stool test for occult blood, endoscopy, and enema X-ray examination). When the endoscopy is chosen from the pull-down menu with the input interface, the searching portion 30 displays "endoscopy" in the section of the examination item in combination with "large-intestine cancer" and the disease-development probability "3%." Furthermore, in combination with the above, the searching portion 30 displays "A" as the examination-accuracy rank R of the endoscopy.

Further, the searching portion 30 displays in a section of difference in price, as well as the combination of the disease i and the chosen examination item. The difference in cost Ce between the examination item associated with the highest examination-accuracy rank R and the chosen examination item is displayed in this section of difference in price. The searching portion 30 reads out, from the examination-item database 31, the cost Ce of the examination item associated with the highest examination-accuracy rank R and the cost Ce of the chosen examination item to compute the difference therebetween, and displays the difference in the section of difference in price.

For example, in the examination-item database 31, the stool test for occult blood is associated with 8,000 yen as the cost Ce, and the endoscopy is associated with 10,000 yen as the cost Ce. The searching portion 30 reads out the 8,000 yen and 10,000 yen from the examination-item database 31 to find the difference therebetween, and displays "+2,000 yen" in the section of difference in price, which indicates that it costs 2,000 yen more.

According to the present embodiment, it is possible in principle to perform the optimal examination for each individual from the viewpoint of the disease-development probability versus the cost, and further, it is possible to change examination planning with high flexibility in consideration of the examination accuracy, individual circumstances and so on.

Incidentally, in the calculation of the difference in price, the searching portion 30 may take and display the difference of the cost Ce between the expected value of the expenditure necessary when the disease i develops, which has been generated by the criterion-generating portion 20, and the chosen examination item.

Fourth Embodiment

An examination-item-selection method according to a fourth embodiment of the present invention is explained. The examination-item-selection method according to the fourth embodiment is to select examination items corresponding to a predetermined group of diseases. The criterion of selection is an expected value of the total expenditure necessary when the predetermined group of diseases develops. A combination of examination items that requires the cost closest to this expected value of the total expenditure is then selected.

FIG. 15 is a flowchart that shows an operation of selecting an examination item according to the fourth embodiment. First, the probability-calculating portion 10 calculates, for each of the predetermined diseases i that are previously designated, the disease-development probability $e_i^{(t)}$ (S71). The predetermined diseases i are pre-stored. Alternatively, the diseases can be chosen with the input interface. The criterion-generating portion 20 calculates an expected value of the expenditure necessary when each of the predetermined diseases i develops, by using the calculated disease-development probability $e_i^{(t)}$ (S72). The criterion-generating portion 20 then adds up the calculated expected values of the diseases i to obtain an expected value of the total expenditure necessary when the predetermined group of diseases develops (S73).

When the expected value of the total expenditure is calculated, the searching portion 30 reads out, from the examination-item database 31, all the costs Ce of the examination items associated with the respective diseases i included in the pre-designated group of diseases (S74). For all combinations of the examination items associated with each of the diseases i, the searching portion 30 calculates the total cost Ce of each of the combinations (S75). The searching portion 30 then compares the calculated total cost Ce of each of the combinations with the expected value of the total expenditure, and picks out the total cost Ce with the smallest absolute value of difference (S76).

After picking out the total cost Ce having the smallest absolute value of difference, the searching portion 30 displays the examination items corresponding to the selected total cost Ce, on the monitor (S77). For each disease i in the predetermined group of diseases, the calculated disease-development probability and the selected examination item are displayed so as to correspond to one another.

FIG. 16 is a diagram that shows the examination-item-selection result displayed by the examination-item-selection device 1 in this fourth embodiment. In a case where angina pectoris, diabetes and large intestine cancer are set as a predetermined group of diseases, the examination-item-selection device 1 refers to the development probabilities of these diseases to calculate the expected value of the expenditure for each of the diseases, and adds up the calculated expected values. For example, in a case where the expected value of the expenditure for angina pectoris is 12,000 yen, the expected value of the expenditure for diabetes is 5,000 yen and the expected value of the expenditure for large intestine cancer is 10,000 yen, the expected value of the total expenditure is the total value of 27,000 yen. Then, one of the examination items for angina pectoris, one of the examination items for diabetes and one of the examination items for large-intestine cancer are chosen and combined, and the total cost Ce of the combination is calculated. The combination and the calculation of the total cost Ce are performed for all combinational patterns. A combination of the total cost Ce with the smallest absolute value of difference from the expected value of the total expenditure is searched out. As a result of the search, a combination of the examination item A for angina pectoris, the examination item B for diabetes and the examination item C for large intestine cancer is displayed. In this combination, the total cost Ce is 27,000 yen. Although the cost of the examination item A for angina pectoris is over the expected value for angina pectoris, the difference from the expected value of the total expenditure is zero.

Fifth Embodiment

Figure 17:
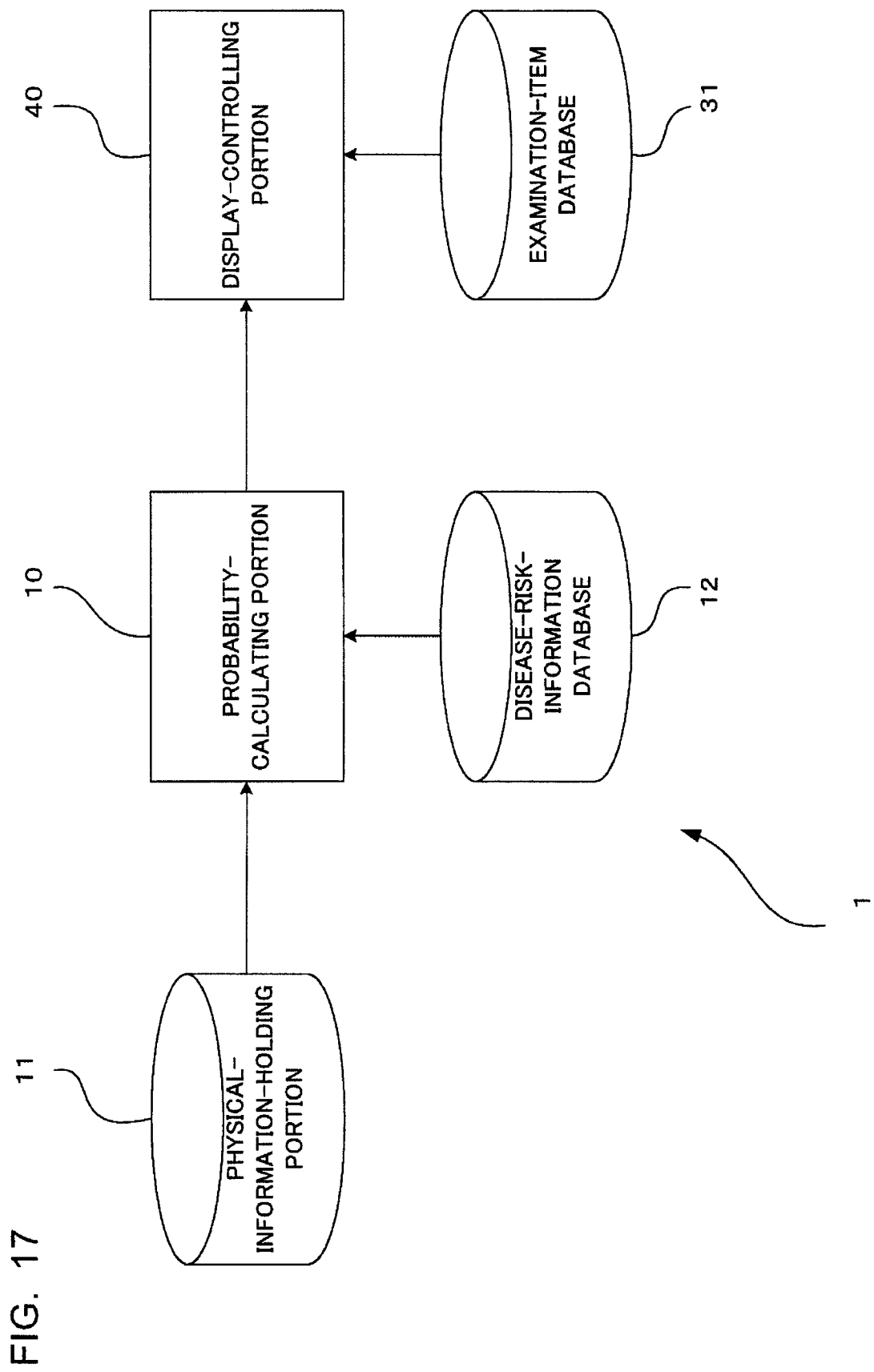
FIG. 17 is a diagram that shows a configuration of an examination-item-selection device according to a fifth embodiment.

The examination-item-selection method according to a fifth embodiment of the present invention is explained. FIG. 17 shows a configuration of the examination-item-selection device 1 according to the present embodiment. The examination-item-selection device 1 according to the present embodiment comprises a physical-information-holding portion 11, a disease-risk-information database 12 and a probability-calculating portion 10, in order to calculate the disease-development probability by executing a program. In addition, the device comprises an examination-item database 31 and a display-controlling portion 40, in order to assist the selection of the examination item. The examination-item-selection device 1 calculates the disease-development probability in a statistical approach by using the disease-risk information from the physical information, and displays this disease-development probability and the examination item for examining the disease side by side. As shown in FIG. 18, the examination-item database 31 stores, for each disease i, various examination items for examining the disease, and further stores the cost Ce incurred for each examination item, the examination-accuracy rank R, the reference information Fi of the disease i, and the reference information Fe of each examination item so as to be associated with one other.

When the disease-development probability of the disease i is calculated, the display-controlling portion 40 extracts, from the examination-item database 31, the examination item associated with the disease i, the cost Ce of the examination item, the examination-accuracy rank R, the reference information Fi of the disease i, and the reference information Fe of the examination item, and causes the monitor to display them simultaneously in pair with the calculated disease-development probability.

Figure 19:
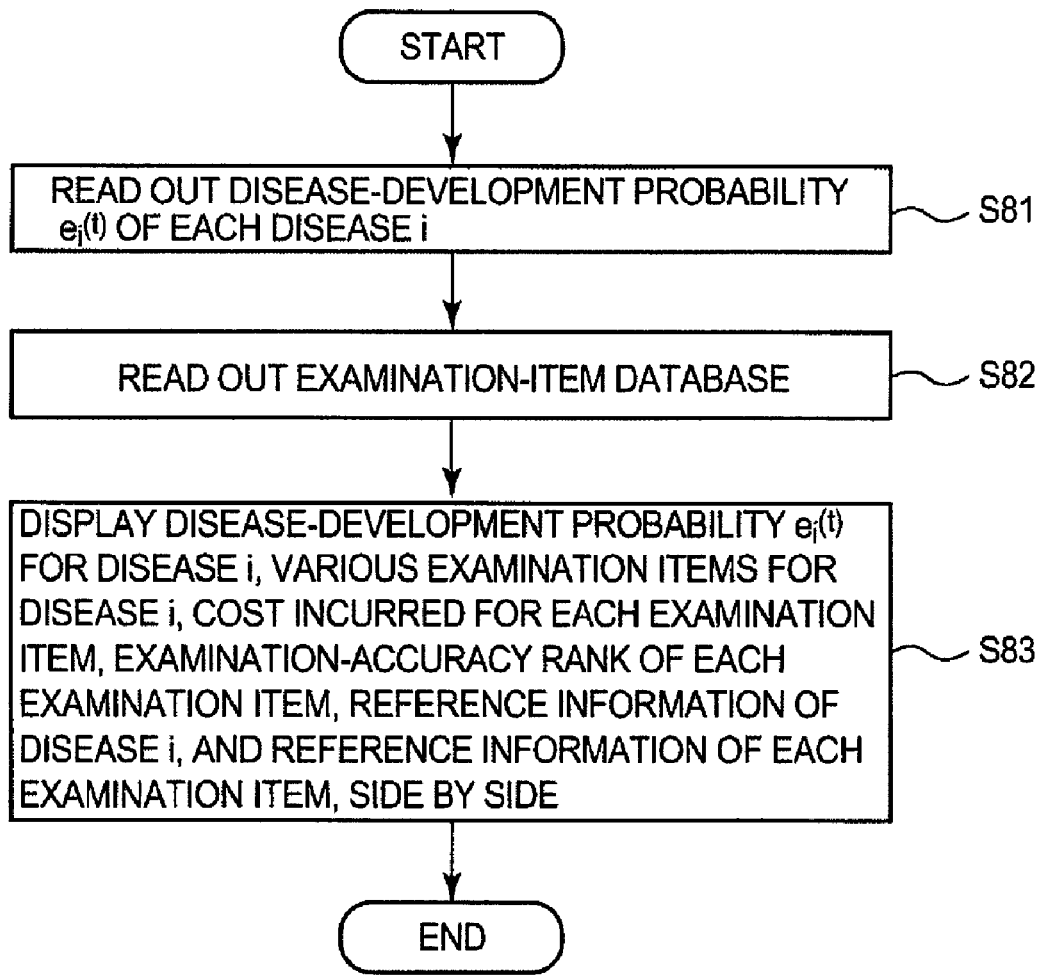
FIG. 19 is a flowchart that shows an operation of displaying an examination item according to the fifth embodiment.

FIG. 19 is a flowchart that shows an operation of displaying the examination item by this display-controlling portion 40. First, the display-controlling portion 40 reads out the disease-development probability $e_i^{(t)}$ of each disease i calculated by the probability-calculating portion 10 (S81), and then reads out the examination-item database 31 (S82). Upon reading out the disease-development probability $e_i^{(t)}$ and the examination-item database 31, the display-controlling portion 40 causes the monitor to display the disease-development probability $e_i^{(t)}$ for the disease i, the examination item for the disease i in the examination-item database 31, the cost Ce incurred for the examination item, the examination-accuracy rank R of the examination item, the reference information Fi of the disease i, and the reference information Fe of the examination item, side by side (S83).

FIG. 20 is a diagram showing a screen on which the disease-development probability and the examination items for examining the disease are displayed side by side. The monitor displays the disease-development probability $e_i^{(t)}$, the examination item associated with the disease i for which the disease-development probability has been calculated, the cost Ce, the examination-accuracy rank R, and the reference information Fi and Fe, side by side. The display-controlling portion 40 extracts, from the examination-item database 31, the examination item, the cost Ce, the examination-accuracy rank R and the reference information Fi and Fe that are stored relating to the disease i. On this screen, a radio button is displayed near each display area of the examination item. By checking the radio button corresponding to one examination item for each disease i by using the input interface, the final decision on the examination item is made.

Thus, the examination-item-selection device according to the present embodiment displays all of the examination items capable of examining the disease i and displays simultaneously the disease-development probability i, the cost Ce, the examination-accuracy rank R, and the reference information Fi and Fe. This enables the user of the device to select an examination item to undergo with reference to the disease-development probability i, the cost Ce, the examination-accuracy rank R, and the reference information Fi and Fe, and enables the examination-item-selection device 1 to present a plurality of suggestions of examination items capable of examining the disease i and to assist the selection of the examination item with each piece of reference information.

Sixth Embodiment

The examination-item-selection method according to the sixth embodiment of the present invention is explained. The examination-item-selection device 1 is capable of selecting an examination item by using any of the examination-item-selection methods according to the first, second, and fifth embodiments.

Figure 21:
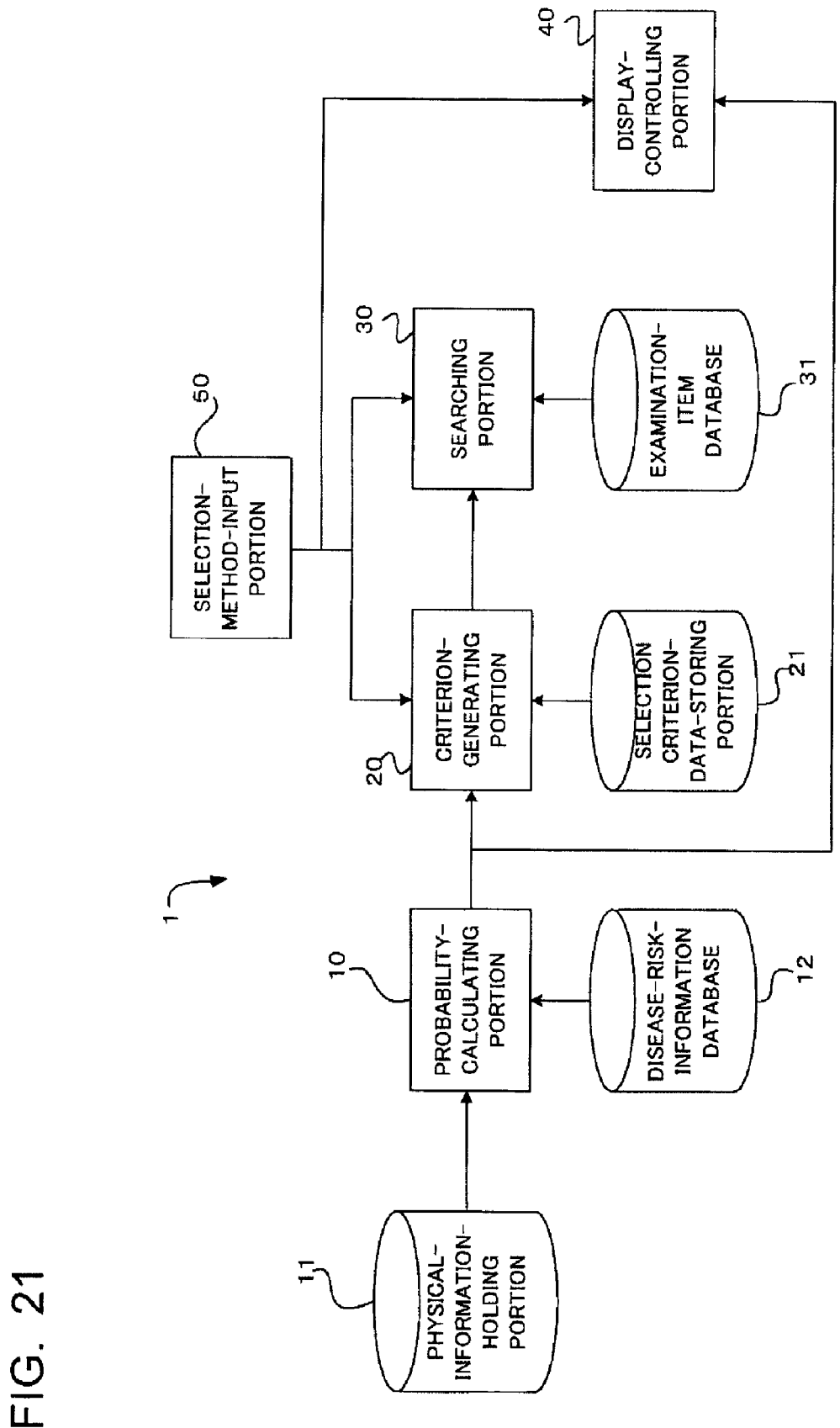
FIG. 21 is a block diagram that shows a configuration of the examination-item-selection device according to a sixth embodiment.

FIG. 21 is a block diagram that shows a configuration of the examination-item-selection device 1 according to the present embodiment. As shown in FIG. 21, the examination-item-selection device 1 of the present embodiment materializes a physical-information-holding portion 11, a disease-risk-information database 12 and a probability-calculating portion 10, in order to calculate the disease-development probability by executing a program. In addition, the device comprises a selection criterion-data-storing portion 21, a criterion-generating portion 20, an examination-item database 31, a searching portion 30, a display-controlling portion 40 and a selection-method-input portion 50, as a selecting part for selecting an examination item.

The selection-method-input portion 50 includes an input interface such as a mouse and a keyboard. A user of the examination-item-selection device 1 inputs an instruction of a method for selecting an examination item into this selection-method-input portion 50. When the method for selecting an examination item is inputted, the selection-method-input portion 50 inputs signals indicated in the inputted selection method, into the criterion-generating portion 20 and the searching portion 30 or the display-controlling portion 40. The criterion-generating portion 20 and the searching portion 30 or the display-controlling portion 40 conduct one process of the selection methods chosen from among the disease-development probability versus the examination accuracy, the disease-development probability versus the cost, and the simultaneous display of the examination item capable of examining the disease i and the disease-development probability, according to the first, second and fifth embodiments. The selection-criterion information is generated in the selection method that has been instructed by the user inputting into the selection-method-input portion. The examination-item database 31 encompasses all data items of the first, second and fifth embodiments. The selection criterion-data-storing portion 21 stores the selection criterion data of both the first embodiment and the second embodiment.

Figure 22:
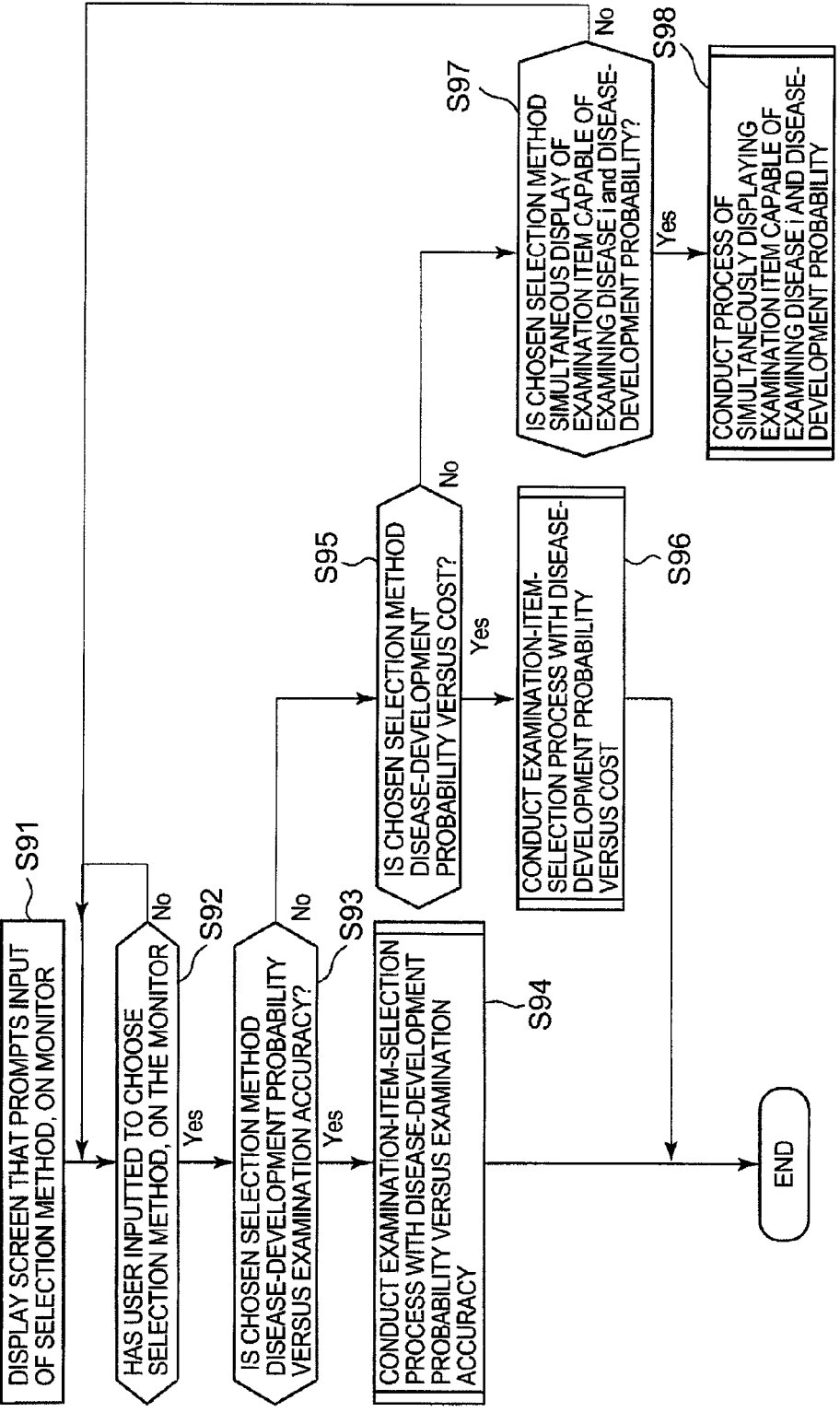
FIG. 22 is a flowchart that shows an operation related to choice of a selection method according to the sixth embodiment.

FIG. 22 is a flowchart that shows an operation of chousing a selection method. First, the selection-method-input portion 50 displays, on the monitor, a display screen that prompts the user to input a selection method (S91). The user inputs to choose a selection method by using the input interface while looking at the display screen displayed on the monitor (S92). When the user inputs to choose a selection method (S92, Yes) and the chosen selection method is the disease-development probability versus the examination accuracy (S93, Yes), the selection-method-input portion 50, after the disease-development probability is calculated, causes the criterion-generating portion 20 and the searching portion 30 to conduct the examination-item-selection process with the disease-development probability versus the examination accuracy according to the first embodiment (S94).

When the chosen selection method is the disease-development probability versus the cost (S95, Yes), the selection-method-input portion 50, after the disease-development probability is calculated, causes the criterion-generating portion 20 and the searching portion 30 to conduct the examination-item-selection process with the disease-development probability versus the cost according to the second embodiment (S96).

When the chosen selection method is the simultaneous display of the examination item capable of examining the disease i and the disease-development probability (S97, Yes), the selection-method-input portion 50, after the disease-development probability is calculated, causes the display-controlling portion 40 to conduct a process of simultaneously displaying the examination item capable of examining the disease i and the disease-development probability according to the fifth embodiment (S98).

Figure 23:
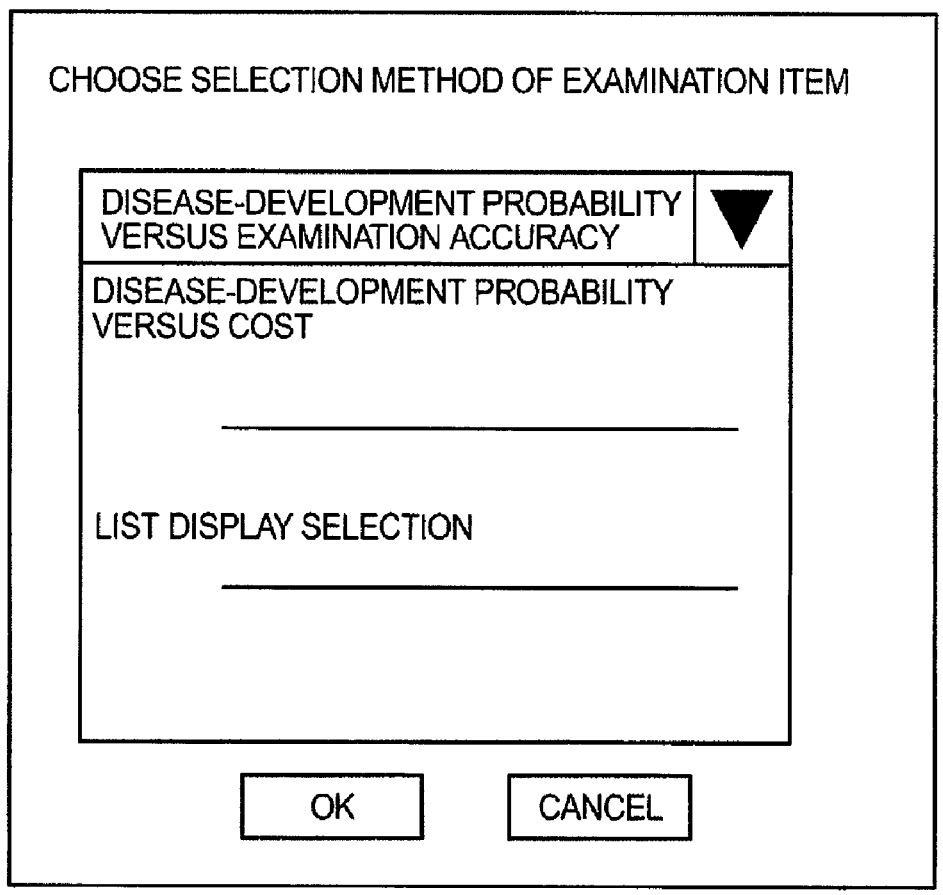
FIG. 23 is a diagram that shows a display screen to be displayed on a monitor at the time of choice of a selection method.

FIG. 23 is a diagram that shows a display screen displayed on the monitor when a selection method is selected with the selection-method-input portion 50. The display screen for choosing a selection method is displayed on the monitor at least before the generation of the criteria-selection information of the first and second embodiments or the search by the searching portion 30 of the fifth embodiment. A pull-down input field for choosing a selection method is displayed on the display screen. In the pull-down input field, a string representing the disease-development probability versus the examination accuracy, a string representing the disease-development probability versus the cost, and a string representing simultaneous display of an examination item capable of examining a predetermined disease, the attributes of the examination item and the disease-development probability are displayed alongside in a selectable manner. The user inputs the choice of any selection method into the selection-method-input portion 50, thereby deciding the selection method for selecting an examination item. After the disease-development probability is calculated, the criterion-generating portion 20 and the searching portion 30 conduct any process in the selection method with the disease-development probability versus the examination accuracy, with the disease-development probability versus the cost, or with the simultaneous display of the examination item capable of examining a predetermined disease, the attributes of the examination item and the disease-development probability, in accordance with the inputted selection method.

Thus, the examination-item-selection device 1 according to the sixth embodiment can choose various selection methods, so that it becomes possible to select an examination item that further reflect the needs of the individual attempting to undergo examination.

What is claimed is:

1. A medical information processing device, comprising:
   a disease-risk calculator configured to read out physical information indicating a physical state of a subject, and to conduct a calculation process using the physical information, so as to calculate a disease-development probability for each of different diseases;
   a non-transitory memory configured to store, for each of the different diseases, (1) a treatment cost that is necessary when the disease develops, and (2) at least one examination item and, for each examination item of the at least one examination item, a corresponding examination cost;
   a criterion generator configured to multiply, for each of the different diseases, the disease-development probability by the treatment cost to determine an expected value of expenditure for the corresponding disease; and
   a searching part configured to search, for each of the different diseases, for an examination item in the memory having an examination cost below the determined expected value of expenditure by comparing the determined expected value of expenditure with the examination cost of the examination item for the corresponding disease.

2. The medical information processing device according to claim 1, further comprising:
   a reference-information-storing part configured to store at least one of reference information on each disease and reference information on the examination item; and
   a display configured to display, when a plurality of examination items are searched out by the searching part, at least one of the reference information on each disease and the reference information on the examination items so as to correspond to the searched-out examination items.

3. The medical information processing device according to claim 1, further comprising:
   an input part configured to choose the examination item; and
   a display configured to display the examination item chosen by the input part, wherein:
   the searching part calculates a difference in cost between the examination item chosen with the input part and the searched-out examination item; and
   the display displays the difference in cost along with the chosen examination item.

4. The medical information processing device according to claim 1, further comprising:
   an input part configured to choose another examination item in addition to the searched-out examination item; and
   a display configured to display the examination item chosen by the input part, wherein:
   the searching part calculates a difference in cost between either the searched-out examination item or the examination item chosen with the input part and the determined expected value; and the display displays the difference in cost along with the searched-out examination item or the chosen examination item.

5. The medical information processing device according to claim 1, wherein the searching part calculates a total examination cost for all combination patterns of examination items, each examination item being chosen from among the examination items capable of examining each disease, and searches for a combination pattern of examination items in which a difference in absolute value between the total of the determined expected value and the total examination cost is below a predetermined threshold.

6. The medical information processing device of claim 1, wherein the searching part is further configured to, for each of the different diseases, select the examination item having a highest examination accuracy rank, when the searching part determines that a plurality of examination items have a corresponding examination cost below the determined expected value of expenditure.

7. A medical information processing method in which an examination-item database storing, for each of different diseases of a plurality of diseases, (1) a treatment cost that is necessary when the disease develops, and (2) at least one examination item and, for each examination item of the at least one examination item, a corresponding examination cost is prepared, the medical information processing method being implemented by a processor programmed as a medical information processing device, the method comprising:

reading out physical information indicating a physical state of a subject and conducting a calculation process using the physical information, so as to calculate a disease-development probability for each of the different diseases;

multiplying, for each of the different diseases, the disease-development probability by the treatment cost to determine an expected value of expenditure for the corresponding disease; and searching, by the medical information processing device, for each of the different diseases, for an examination item in the database having an examination cost below the determined expected value of expenditure by comparing the determined expected value of expenditure with the examination cost of the examination item for the corresponding disease.

\* \* \* \* \*